(12) United States Patent
Anselm et al.

(10) Patent No.: US 7,550,487 B2
(45) Date of Patent: Jun. 23, 2009

(54) PYRROLIDINE-3,4-DICARBOXAMIDE DERIVATIVES

(75) Inventors: Lilli Anselm, Binzen (DE); Katrin Groebke Zbinden, Basel (CH); Wolfgang Haap, Loerrach (DE); Jacques Himber, Guebwiller (FR); Christoph Martin Stahl, Freiburg (DE); Stefan Thomi, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 12 days.

(21) Appl. No.: 11/076,162

(22) Filed: Mar. 9, 2005

(65) Prior Publication Data

US 2005/0215599 A1 Sep. 29, 2005

(30) Foreign Application Priority Data

Mar. 26, 2004 (EP) .................. 04101265

(51) Int. Cl.
*A61K 31/443* (2006.01)
*A61K 31/401* (2006.01)
*C07D 43/02* (2006.01)

(52) U.S. Cl. .................. 514/343; 514/422; 514/423; 546/278.1; 548/517; 548/530

(58) Field of Classification Search .................. 548/226, 548/227, 537, 517, 530; 514/376, 508, 528, 514/334, 343, 423, 422; 546/193, 208, 256, 546/278.4, 279.1, 278.1
See application file for complete search history.

(56) References Cited

U.S. PATENT DOCUMENTS

| 6,429,213 | B1 * | 8/2002 | Xue et al. .................. 514/312 |
| 6,858,626 | B2 * | 2/2005 | Xue et al. .................. 514/312 |
| 7,030,141 | B2 * | 4/2006 | Bigge et al. .................. 514/334 |
| 2003/0139597 | A1 | 7/2003 | Xue et al. |
| 2006/0106016 | A1 | 5/2006 | Boehringer et al. |
| 2006/0142362 | A1 | 6/2006 | Boehringer et al. |
| 2006/0247238 | A1 | 11/2006 | Zbinden et al. |
| 2007/0015812 | A1 | 1/2007 | Boehringer et al. |
| 2007/0049587 | A1 | 3/2007 | Zbinden et al. |
| 2007/0112001 | A1 | 5/2007 | Anselm et al. |
| 2007/0112012 | A1 | 5/2007 | Boehringer et al. |
| 2007/0249683 | A1 | 10/2007 | Zbinden et al. |

FOREIGN PATENT DOCUMENTS

WO WO 02/22575 A1 3/2002
WO WO 03/045912 6/2003

OTHER PUBLICATIONS

Al-Obeidi, F., et al., Expert opinion on Therapeutic Patents, Ashley Publications, GB, vol. 9, pp. 931-953 (1999), XP001000512.
Cheng, Y. C. and Prusoff, W. H., *Relationship Between The Inhibition Constant (Ki) And The Concentration Of Inhibitor Which Causes 50 Per Cent Inhibition ($I_{50}$) Of An Enzymatic Reaction*, Biochem. Pharmacol., vol. 22, pp. 3099-3108 (1973).
Lottenberg et al., *The Action Of Thrombin On Peptide p-Nitroanilide Substrates: Substrate Selectivity And Examination Of Hydrolysis Under Different Reaction Conditions*, Biochim Biophys Acta., vol. 742, pp. 539-557 (1983).
Eadie, G. S., *The Inhibition of Cholinesterase By Physostigmine and Prostigmine*, J. Biol. Chem., vol. 146, pp. 85-93 (1942).
Sarmiento et al., *Chemoenzymatic Preparation Of Non-Racemic N-Boc-Pyrrolidine-3,4-Dicarboxylic Acid 3-Ethyl Esters And Their 4-Hydroxymethyl Deriviatives*, Tetrahedron Asymmetry, vol. 14, pp. 1547-1551 (2003).

* cited by examiner

*Primary Examiner*—Sabiha N. Qazi
(74) *Attorney, Agent, or Firm*—George W. Johnston; Dennis P. Tramaloni; Brian C. Remy

(57) ABSTRACT

The invention is concerned with novel pyrrolidine-3,4-dicarboxamide derivatives of formula (I)

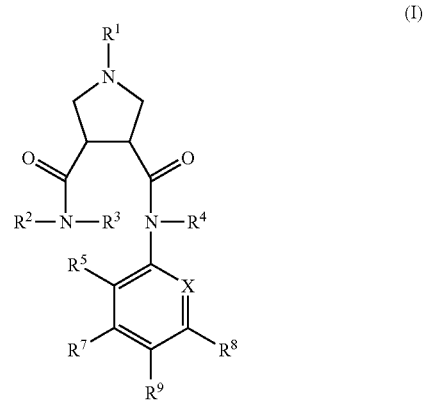

wherein $R^1$ to $R^9$ and X are as defined in the description and in the claims, as well as physiologically acceptable salts thereof. These compounds inhibit the coagulation factor Xa and can be used as medicaments.

30 Claims, No Drawings

PYRROLIDINE-3,4-DICARBOXAMIDE DERIVATIVES

The present invention relates to novel pyrrolidine-3,4-dicarboxamide derivatives, to a process for their manufacture, medicaments containing them and their manufacture as well as the use of these compounds as pharmaceutically active agents.

BACKGROUND OF THE INVENTION

The compounds of formula (I) are active compounds and inhibit the coagulation factor Xa. These compounds consequently influence blood coagulation. They therefore inhibit the formation of thrombi and can be used for the treatment and/or prevention of thrombotic disorders, such as amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. They have potentially benefit in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumour agents.

Other inhibitors of factor Xa, which are not structurally related to the compounds of the present invention, had previously been suggested for the inhibition of the formation of thrombi and for the treatment of related diseases (WO 03/045912). However, there is still a need for novel factor Xa inhibitors which exhibit improved pharmacological properties, e.g. an improved selectivity towards coagulation factor Xa.

The present invention provides the novel compounds of formula (I) which are factor Xa inhibitors The compounds of the present invention unexpectedly inhibit coagulation factor Xa and also exhibit improved pharmacological properties compared to other compounds already known in the art.

SUMMARY OF THE INVENTION

The invention is concerned with novel pyrrolidine-3,4-dicarboxamide derivatives of the formula (I)

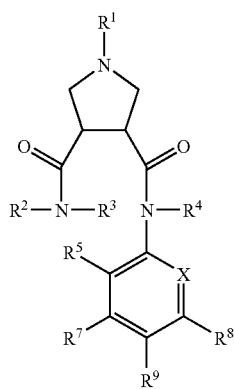

and the pharmaceutically acceptable salts thereof, wherein X, $R^1$, $R^2$, $R^3$, $R^4$, $R^5$, $R^7$, $R^8$ and $R^9$ as described in this application. These compounds are believed to inhibit the coagulation factor Xa and hence inhibit the formulation of thrombi and therefore be used for the treatment and/or prevention of thrombotic disorders.

DETAILED DESCRIPTION OF THE INVENTION

The invention is concerned with novel pyrrolidine-3,4-dicarboxamide derivatives of the formula (I)

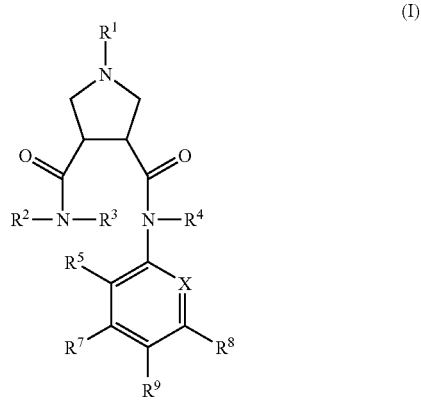

wherein

X is N or C—$R^6$;

$R^1$ is hydrogen, lower-alkyl, cycloalkyl, cycloalkyl-lower-alkyl, fluoro-lower-alkyl, hydroxy-lower-alkyl, CN-lower-alkyl, hydroxy substituted fluoro-lower-alkyl, lower-alkinyl, $R^{10}C(O)$—, $R^{10}OC(O)$—, $N(R^{11},R^{12})C(O)$—, $R^{10}OC(O)$-lower-alkyl, $N(R^{11},R^{12})C(O)$-lower-alkyl, $R^{10}$—$SO_2$, $R^{10}$—$SO_2$-lower-alkyl, $N(R^{11},R^{12})$—$SO_2$, $N(R^{11},R^{12})$—$SO_2$-lower-alkyl, aryl-lower-alkyl, heteroaryl, heteroaryl-lower-alkyl, lower alkoxy-lower alkyl, lower alkoxycarbonyl-cycloalkyl-lower alkyl or heterocyclyl-lower alkyl;

$R^2$ is hydrogen or lower-alkyl;

$R^3$ is aryl, aryl-lower-alkyl, heteroaryl or heteroaryl-lower-alkyl;

$R^4$ is hydrogen, lower-alkyl or hydroxy;

$R^5$, $R^6$, $R^7$ and $R^8$ independently from each other are selected from the group consisting of hydrogen, halogen, lower-alkyl, lower-alkoxy, fluoro-lower-alkyl, fluoro-lower-alkyloxy or CN;

$R^9$ is aryl, heterocyclyl, heteroaryl or, or heterocyclyl-C(O)— or heterocyclyl-$SO_2$—;

$R^{10}$ is hydrogen, lower-alkyl, cycloalkyl, cycloalkyl-lower-alkyl, hydroxy-lower-alkyl, fluoro-lower-alkyl, lower-alkyl-$SO_2$-lower-alkyl, aryl, aryl-lower-alkyl, heteroaryl, or heteroaryl-lower-alkyl or heterocyclyl;

$R^{11}$ and $R^{12}$ independently from each other are selected from the group consisting of hydrogen, lower-alkyl, hydroxy-lower-alkyl, fluoro-lower-alkyl, cycloalkyl, cycloalkyl-lower-alkyl, aryl, aryl-lower-alkyl, heteroaryl and heteroaryl-lower-alkyl; or $R^{11}$ and $R^{12}$, together with the nitrogen atom to which they are attached, form a heterocyclic ring selected from the group consisting of piperidinyl, piperazinyl, morpholinyl, pyrrolidinyl, pyrrolinyl or azetidinyl, which heterocyclic ring can optionally be substituted with lower-alkyl, halogen or hydroxy;

and pharmaceutically acceptable salts thereof.

Further, the invention is concerned with a process for the manufacture of the above compounds, pharmaceutical preparations which contain such compounds as well as the use of these compounds for the production of pharmaceutical preparations.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, i-butyl, t-butyl. Lower-alkyl groups can optionally be substituted, e.g. by hydroxy or CN. Such substituted lower-alkyl-groups are referred to as "hydroxy-lower-alkyl" or "CN-lower-alkyl" respectively. Other possible optional substituents are e.g. halogen. Unsubstituted lower-alkyl groups are preferred.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H—CF_2$.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "thio-alkoxy" refers to the group R'—S—, wherein R' is an alkyl. The term "thio-lower-alkoxy" refers to the group R'—S—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H—CF_2$—O.

The term "alkenyl", alone or in combination with other groups, stands for a straight-chain or branched hydrocarbon residue comprising an olefinic bond and 2 to 20, preferably 2 to 16 carbon atoms, more preferably 2 to 10 carbon atoms. Lower-alkenyl groups as described below also are preferred alkenyl groups. The term "lower-alkenyl" refers to a straight-chain or branched hydrocarbon residue comprising an olefinic bond and 2 to 7, preferably 2 to 4 carbon atoms, such as e.g. 2-propenyl.

The term "alkinyl", alone or in combination with other groups, stands for a straight-chain or branched hydrocarbon residue comprising a tripple bond and up to 20, preferably up to 16 carbon atoms. The term "lower-alkinyl" refers to a straight-chain or branched hydrocarbon residue comprising a tripple bond and 2 to 7, preferably 2 to 4 carbon atoms, such as e.g. 2-propinyl. Lower-alkinyl groups can be substituted, e.g. by hydroxy.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl" relates to the phenyl or naphthyl group, preferably the phenyl group, which can optionally be substituted by 1 to 5, preferably 1 to 3, substituents independently selected from the group consisting of lower-alkenyl, lower-alkinyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$, preferably selected from the group consisting of lower-alkenyl, lower-alkinyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy and, lower-alkyl which can optionally be substituted with halogen, hydroxy, $NH_2$, N(H, lower-alkyl) or N(lower-alkyl)$_2$. Preferred substituents are halogen, lower-alkoxy, fluoro-lower-alkoxy, thio-lower-alkoxy, and amino.

The term "heterocyclyl" as used herein denotes non-aromatic monocyclic heterocycles with 4 or 6 ring members, which comprise 1, 2 or 3 hetero atoms selected from nitrogen, oxygen and sulfur. A hetero atom can be —SO— or —SO$_2$—. Examples of suitable heterocycles are pyrrolidinyl, oxopyrrolidinyl, isoxazolidinyl, isoxazolinyl, pyrrolinyl, imidazolidinyl, imidazolinyl, pyrazolidinyl, pyrazolinyl, piperidinyl, 2-oxo-piperidinyl, 3-oxo-morpholinyl, 2-oxo-piperazinyl, 2-oxo-oxazolidinyl, 2-oxo-azetidinyl, piperazinyl, morpholinyl, pyranyl, tetrahydropyranyl, 4,5-dihydro-oxazolyl, 4,5-dihydro-thiazolyl. Preferred heterocycles are, morpholinyl, 3-oxo-morpholinyl, 2-oxo-piperazinyl and 2-oxo-piperidinyl. A heterocyclyl group may have a substitution pattern as described earlier in connection with the term "aryl". One or two ring member carbon atoms of a heterocyclyl group may be replaced with a carbonyl group.

The term "heteroaryl" refers to an aromatic 5 to 6 membered monocyclic ring or 9 to 10 membered bicyclic ring which can comprise 1, 2, 3 or 4, preferably 1, 2 or 3 atoms selected from nitrogen, oxygen and/or sulphur, such as furyl, pyridyl, pyridazinyl, oxo-pyridazinyl, pyrimidinyl, 2-oxo-pyridinyl, 2-oxo-pyrimidinyl pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, Preferred heteroaryl groups are 2-oxo-pyridinyl, 2-oxo-pyrimidinyl, pyridinyl, and indolyl. A heteroaryl group may have a substitution pattern as described earlier in connection with the term "aryl".

Preferred substituents are halogen, lower-alkyl, lower-alkoxy or CN. One or two ring member carbon atoms of a heteroaryl group may be replaced with a carbonyl group.

The term "mono-lower alkyl substituted amino" and "di-lower alkyl substituted amino" refer to —NHR and —NRR' respectively, wherein R and R' independent from each other are lower alkyl.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammoniumsalt. The term "pharmaceutically acceptable salts" also refers to such salts. Acid addition salts as described above are preferred.

Preferably $R^1$ is hydrogen, lower alkyl, cycloalkyl, cycloalkyl-lower alkyl, fluoro-lower alkyl, hydroxy-lower alkyl, CN-lower alkyl, hydroxy substituted fluoro-lower alkyl, lower alkinyl, $R^{10}C(O)$—, $R^{10}OC(O)$—, $N(R^{11},R^{12})C(O)$—, $R^{10}OC(O)$—lower alkyl, $N(R^{11},R^{12})C(O)$-lower alkyl, $R^{10}$—$SO_2$, $R^{10}$—$SO_2$-lower alkyl, $N(R^{11},R^{12})$—$SO_2$, $N(R^{11},R^{12})$—$SO_2$-lower alkyl, aryl-lower alkyl, heteroaryl or heteroaryl-lower alkyl;

$R^{10}$ is hydrogen, lower alkyl, cycloalkyl, cycloalkyl-lower alkyl, hydroxy-lower alkyl, fluoro-lower alkyl, lower alkyl-$SO_2$-lower alkyl, aryl, aryl-lower alkyl, heteroaryl or heteroaryl-lower alkyl.

Compounds of formula (I) are individually preferred and physiologically acceptable salts thereof are individually preferred, with the compounds of formula (I) being particularly preferred.

The compounds of formula (I) have at least two asymmetric C atoms and can therefore exist as an enantiomeric mixture, diastereomeric mixture or as optically pure compounds. Preferred are compounds which are 3R,4R-pyrrolidine-3,4-dicarboxylic acid derivatives. One preferred embodiment of the present invention therefore relates to compounds of formula (I) as defined above, characterised by formula (Ia)

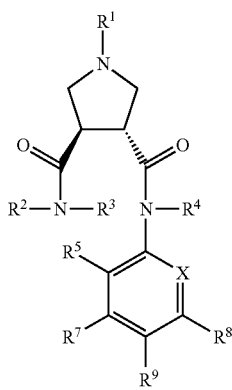

(Ia)

wherein $R^1$, $R^2$, $R^3$, $R^4$, $R^5$, $R^7$, $R^8$, $R^9$ and X are as defined above, and pharmaceutically acceptable salts thereof.

Preferred compounds of formula (I) are those, wherein $R^1$ is hydrogen, lower-alkyl, fluoro-lower-alkyl, hydroxy-lower-alkyl, CN-lower-alkyl, HC(O)—, lower-alkyl-C(O)—, lower-alkoxy-C(O)—, lower-alkoxy-C(O)-lower-alkyl, $NH_2$—C(O)-lower-alkyl, lower-alkyl-NH—C(O)-lower-alkyl, $NH_2$—$SO_2$, lower-alkyl-$SO_2$, fluoro-lower-alkyl-$SO_2$, N(lower-alkyl)$_2$—$SO_2$ or pyrrolidino-C(O)—. Compounds as defined above, wherein $R^1$ is lower-alkyl, fluoro-lower-alkyl, lower-alkyl-$SO_2$, fluoro-lower-alkyl-$SO_2$, N(lower-alkyl)$_2$—$SO_2$, lower-alkoxy-C(O)— or HC(O)—, are more preferred, with those compounds as defined above, wherein $R^1$ is 2,2-difluoro-ethyl, ethanesulfonyl, methanesulfonyl, propylsulfonyl, isopropylsulfonyl, 2,2,2-trifluoro-ethylsulfonyl, isopropyl, N(CH$_3$)$_2$—$SO_2$, ethoxy-carbonyl, or formyl, being particularly preferred.

In another preferred embodiment of the present invention, $R^2$ is hydrogen. Furthermore, compounds as defined above, wherein $R^3$ is phenyl optionally substituted with 1 to 3 substituents selected from the group consisting of halogen, $NH_2$, lower-alkoxy and fluoro-lower-alkoxy, or $R^3$ is benzyl optionally substituted with halogen, or $R^3$ is pyridinyl optionally substituted with halogen, or $R^3$ is indolyl, are preferred. Particularly preferred are those compounds, wherein $R^3$ is phenyl substituted with halogen or $R^3$ is pyridinyl substituted with halogen. Most preferably, $R^3$ is 4-chloro-phenyl or 5-chloro-pyridin-2-yl.

In a further preferred embodiment of the present invention, $R^4$ is hydrogen. Another preferred embodiment of the present invention relates to compounds of formula (I) as defined above, wherein X is C—$R^6$ and $R^6$ is as defined above. Preferably, X is C—$R^6$ and $R^5$, $R^6$, $R^7$ and $R^8$ independently from each other are selected from the group consisting of hydrogen and halogen. More preferably, X is C—$R^6$, $R^6$ is halogen, $R^5$, $R^7$ and $R^8$ are hydrogen. Most preferably, X is C—$R^6$, $R^6$ is fluorine, $R^5$, $R^7$ and $R^8$ are hydrogen.

The invention especially embraces compounds of formula (I) as described above, wherein $R^9$ is aryl, heterocyclyl or heteroaryl. Those compounds, wherein $R^9$ is heteroaryl, are preferred. A preferred heteroaryl group for $R^9$ is one selected from the group consisting of furyl, pyridyl, pyridazinyl, oxo-pyridazinyl, pyrimidinyl, 2-oxo-pyridinyl, 2-oxo-pyrimidinyl pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl and indazolyl. 2-oxo-2H-pyridin-1-yl is particularly preferred.

In particular, preferred compounds are the compounds of formula (I) described in the examples as individual compounds as well as pharmaceutically acceptable salts thereof.

Preferred compounds of formula (I) are those selected from the group consisting of (3R,4R)-1-(2,2,2-Trifluoro-ethyl)-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-(2,2-Difluoro-ethyl)-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Sulfamoyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Sulfamoyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Ethanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-Isopropyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(5-chloro-pyridin-2-yl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(5-chloro-pyridin-2-yl)-amide]4-{[2-fluoro-4-(2-oxo-2H-pyridin-1-yl)-phenyl]-amide},
(3R,4R)-1-Methylcarbamoylmethyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid methyl ester,
(3R,4R)-1-(2-Hydroxy-ethyl)-pyrrolidine-3,4-dicarboxylic acid 3-[(4-chloro-phenyl)-amide]4-{[2-fluoro-4-(2-oxo-2H-pyridin-1-yl)-phenyl]-amide},
trans-(3RS,4RS)-1-Methanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(4-chloro-phenyl)-amide]4-{[2-fluoro-4-(3-methoxy-2-oxo-2H-pyridin-1-yl)-phenyl]-amide},
(3R,4R)-1-Acetyl-pyrrolidine-3,4-dicarboxylic acid 3-[(4-chloro-phenyl)-amide]4-{[4-(3-methoxy-2-oxo-2H-pyridin-1-yl)-phenyl]-amide},
trans-(3RS,4RS)-1-Cyanomethyl-pyrrolidine-3,4-dicarboxylic acid 3-[(4-chloro-phenyl)-amide]4-{[2-fluoro-4-(2-oxo-2H-pyridin-1-yl)-phenyl]-amide},
trans-(3RS,4RS)-1-Carbamoylmethyl-pyrrolidine-3,4-dicarboxylic acid 3-[(4-chloro-phenyl)-amide]4-{[2-fluoro-4-(2-oxo-2H-pyridin-1-yl)-phenyl]-amide},
trans-(3RS,4RS)-1-(3,3,3-Trifluoro-propyl)-pyrrolidine-3,4-dicarboxylic acid 3-[(4-chloro-phenyl) -amide]4-{[2-fluoro-4-(2-oxo-2H-pyridin-1-yl)-phenyl]-amide},
(3R,4R)-1-Formyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(4-chloro-3-fluoro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(4-chloro-2-fluoro-phenyl)-amide]4-{[2-fluoro-4-(2-oxo-2H-pyridin-1-yl)-phenyl]-amide},
trans-(3RS,4RS)-{3-(4-Chloro-phenylcarbamoyl)-4-[2-fluoro-4-(2-oxo-2H-pyridin-1-yl)-phenylcarbamoyl]-pyrrolidin-1-yl}-acetic acid ethyl ester,
(3R,4R)-1-Methanesulfonyl-pyrrolidine-3,4-dicarboxylic acid 3-[(3-fluoro-4-methoxy-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-{[2-fluoro-4-(2-oxo-2H-pyridin-1-yl)-phenyl]-amide}4-[(1H-indol-5-yl)-amide],
(3R,4R)-1-Methanesulfonyl-pyrrolidine-3,4-dicarboxylic acid 3-[(2-amino-4-chloro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-{[2-fluoro-4-(2-oxo-2H-pyridin-1-yl)-phenyl]-amide}4-[(4-methoxy-phenyl)-amide],
(3R,4R)-1-Methanesulfonyl-pyrrolidine-3,4-dicarboxylic acid 3-[(4-chloro-phenyl)-amide]4-[(3-fluoro-4-morpholin-4-yl-phenyl)-amide],
(3S,4S)-1-Methanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(3-chloro-4-methoxy-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(4-chloro-phenyl)-methyl-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-{[2-fluoro-4-(2-oxo-2H-pyridin-1-yl)-phenyl]-amide}4-[(1H-indazol-5-yl)-amide],
(3R,4R)-1-Methanesulfonyl-pyrrolidine-3,4-dicarboxylic acid 3-[(4-chloro-phenyl)-amide]4-[(3-fluoro-4-[1,2,4]triazol-1-yl-phenyl)-hydroxy-amide],
(3R,4R)-1-Methanesulfonyl-pyrrolidine-3,4-dicarboxylic acid 3-[(4-chloro-phenyl)-amide]4-{[3-fluoro-4-(2-methyl-imidazol-1-yl)-phenyl]-amide},
(3R,4R)-Pyrrolidine-3,4-dicarboxylic acid 3-[(4-chloro-phenyl)-amide]4-[(3-fluoro-2'-methylsulfanyl-biphenyl-4-yl)-amide],
(3R,4R)-1-Methanesulfonyl-pyrrolidine-3,4-dicarboxylic acid 3-{[2-fluoro-4-(2-oxo-2H-pyridin-1-yl)-phenyl]-amide}4-[(4-methoxy-phenyl)-methyl-amide],
(3R,4R)-1-Methanesulfonyl-pyrrolidine-3,4-dicarboxylic acid 3-(4-chloro-benzylamide) 4-{[2-fluoro-4-(2-oxo-2H-pyridin-1-yl)-phenyl]-amide},
(3R,4R)-1-Methanesulfonyl-pyrrolidine-3,4-dicarboxylic acid 3-{[2-fluoro-4-(2-oxo-2H-pyridin-1-yl)-phenyl]-amide}4-[(4-trifluoromethoxy-phenyl)-amide],
(3R,4R)-1-(Propane-2-sulfonyl)-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-(2,2,2-Trifluoro-ethanesulfonyl)-pyrrolidine-3,4-dicarboxylic acid 3-[(4-chloro-phenyl) -amide]4-{[2-fluoro-4-(2-oxo-2H-pyridin-1-yl)-phenyl]-amide},
(3R,4R)-1-Dimethylsulfamoyl-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid ethyl ester,
(3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid propyl ester,
(3R,4R)-1-(Pyrrolidine-1-carbonyl)-pyrrolidine-3,4-dicarboxylic acid 3-[(4-chloro-phenyl)-amide]4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(4-chloro-phenyl)-amide]4-{[2,6-difluoro-4-(2-oxo-2H-pyridin-1-yl)-phenyl]-amide},
(3R,4R)-1-Methanesulfonyl-pyrrolidine-3,4-dicarboxylic acid 3-[(4-chloro-phenyl)-amide]4-{[2-fluoro-4-(6-oxo-6H-pyridazin-1-yl)-phenyl]-amide},
(3R,4R)-1-Methanesulfonyl-pyrrolidine-3,4-dicarboxylic acid 3-[(4-chloro-phenyl)-amide]4-{[2-fluoro-4-(2-oxo-piperidin-1-yl)-phenyl]-amide},
(3R,4R)-1-Propanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide}, and (3R,4R)-1-(2-Fluoro-ethyl)-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-Pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid tert-butyl ester, (3R,4R)-Pyrrolidine-3,4-dicarboxylic acid 3-[(5-chloro-pyridin-2-yl)-amide]4-{[2-fluoro-4-(2-oxo-2H-pyridin-1-yl)-phenyl]-amide}, (3S,4S)-1-Methanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(4-chloro-phenyl)-amide]4-{[4-(2,5-dihydro-pyrrole-1-carbonyl)-phenyl]-amide}, (3R,4R)-1-Methanesulfonyl-pyrrolidine-3,4-dicarboxylic acid 3-[(4-chloro-phenyl)-amide]4-{[3-(morpholine-4-sulfonyl)-phenyl]-amide}, (3R,4R)-1-Methanesulfonyl-pyrrolidine-3,4-dicarboxylic acid 3-[(4-chloro-phenyl)-amide]4-{[3-(4-methyl-piperazine-1-sulfonyl)-phenyl]-amide}, (3R,4R)-1-Methanesulfonyl-pyrrolidine-3,4-dicarboxylic acid 3-[(4-chloro-phenyl)-amide]4-{[4-(morpholine-4-carbonyl)-phenyl]-amide}, (3R,4R)-1-Methanesulfonyl-pyrrolidine-3,4-dicarboxylic acid 3-[(4-chloro-phenyl)-amide]4-{[4-(4-methyl-piperazine-1-carbonyl)-phenyl]-amide};

(3R,4R)-1-Methanesulfonyl-pyrrolidine-3,4-dicarboxylic acid 3-[(4-chloro-phenyl)-amide]4-{[4-(thiomorpholine-4-carbonyl)-phenyl]-amide}, (3R,4R)-1-Methanesulfonyl-pyrrolidine-3,4-dicarboxylic acid 3-[(4-chloro-phenyl)-amide]4-{[4-(4-ethyl-piperazine-1-carbonyl)-phenyl]-amide}, (3R,4R)-1-Methanesulfonyl-pyrrolidine-3,4-dicarboxylic acid 3-[(4-chloro-phenyl)-amide]4-{[4-(4,4-difluoro-piperidine-1-carbonyl)-phenyl]-amide}, (3R,4R)-1-Methanesulfonyl-pyrrolidine-3,4-dicarboxylic acid 3-[(4-chloro-phenyl)-amide]4-{[4-(4-fluoro-piperidine-1-carbonyl)-phenyl]-amide}, (3R,4R)-1-Methanesulfonyl-pyrrolidine-3,4-dicarboxylic acid 3-[(4-chloro-phenyl)-amide]4-{[4-(1-oxy-pyridin-2-yl)-phenyl]-amide}, (3R,4R)-1-(2,2-Difluoroethyl)-pyrrolidine-3,4-dicarboxylic acid 3-[(5-chloro-pyridin-2-yl)-amide]4-{[2-fluoro-4-(2-oxo-2H-pyridin-1-yl)-phenyl]-amide}, (3R,4R)-1-Isopropyl-pyrrolidine-3,4-dicarboxylic acid 3-[(5-chloro-pyridin-2-yl)-amide]4-{[2-fluoro-4-(2-oxo-2H-pyridin-1-yl)-phenyl]-amide} and pharmaceutically acceptable salts thereof.

Particularly preferred compounds of formula (I) are those selected from the group consisting of (3R,4R)-1-(2,2-Difluoro-ethyl)-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Ethanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Isopropyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(5-chloro-pyridin-2-yl)-amide]4-{[2-fluoro-4-(2-oxo-2H-pyridin-1-yl)-phenyl]-amide}, (3R,4R)-1-Formyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-(Propane-2-sulfonyl)-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-(2,2,2-Trifluoro-ethanesulfonyl)-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-Dimethylsulfamoyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid ethyl ester, and (3R,4R)-1-Propanesulfonyl-pyrrolidine-3,4-dicarboxylic acid 3-[(4-chloro-phenyl)-amide]4-{[2-fluoro-4-(2-oxo-2H-pyridin-1-yl)-phenyl]-amide}, (3R,4R)-1-(2,2-Difluoroethyl)-pyrrolidine-3,4-dicarboxylic acid 3-[(5-chloro-pyridin-2-yl)-amide]4-{[2-fluoro-4-(2-oxo-2H-pyridin-1-yl)-phenyl]-amide}, (3R,4R)-1-Isopropyl-pyrrolidine-3,4-dicarboxylic acid 3-[(5-chloro-pyridin-2-yl)-amide]4-{[2-fluoro-4-(2-oxo-2H-pyridin-1-yl)-phenyl]-amide} and pharmaceutically acceptable salts thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (II)

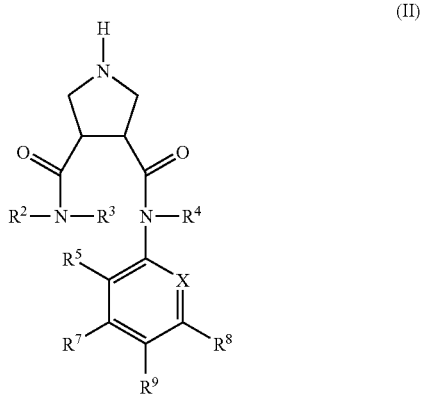

with a compound LG-R$^1$, or reacting a compound of formula (III)

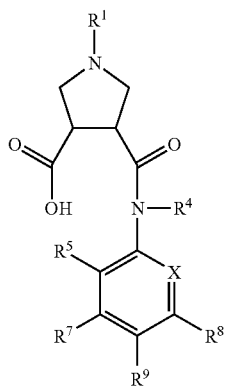

with a compound NHR²R³ or
reacting a compound of formula (IV)

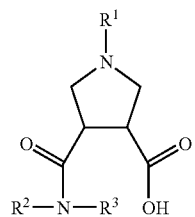

with a compound of formula (V)

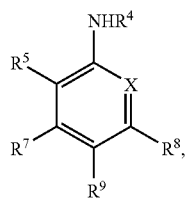

wherein $R^1$, $R^2$, $R^3$, $R^4$, $R^5$, $R^7$, $R^8$, $R^9$, and X have the significances given above and LG is a leaving group.

The reaction of a compound of formula (II) with a compound LG-$R^1$ is conveniently carried out in a solvent such as e.g. dichloromethane, THF, acetonitrile, DMF, DMA, DMSO, NMP etc. with bases like DIEA, triethylamine, pyridine, N-methylmorpholine, $Na_2CO_3$, $K_2CO_3$, $Cs_2CO_3$ etc. Suitable leaving groups are well known in the art, e.g. halogenides, triflates, para-nitrophenolates or -mesylates.

Suitable reaction conditions for the reaction of a compound of formula (III) with a compound NHR²R³ or of a compound of formula (IV) with a compound of formula (V) are well known to the person skilled in the art. Such reactions can be carried out in a solvent such as e.g. dichloromethane, DMF, acetonitrile, THF, NMP, DMA, etc. and in the presence of an activating amide coupling reagent like EDC, DIC, DCC, CDI, TBTU, HBTU, EEDQ, CIP, HOBt, HATU, PyBOP, PyBrOP, BOP, BOP-Cl, TFFH, isobutylcarbamoyl chloride, etc. at a suitable temperature, which can e.g. be chosen in the range of −10° C.-120° C.

Moreover, the invention further relates to another process for the manufacture of compounds of formula (I) as defined above, which process comprises Reacting a compound of formula (VI) or (VIII)

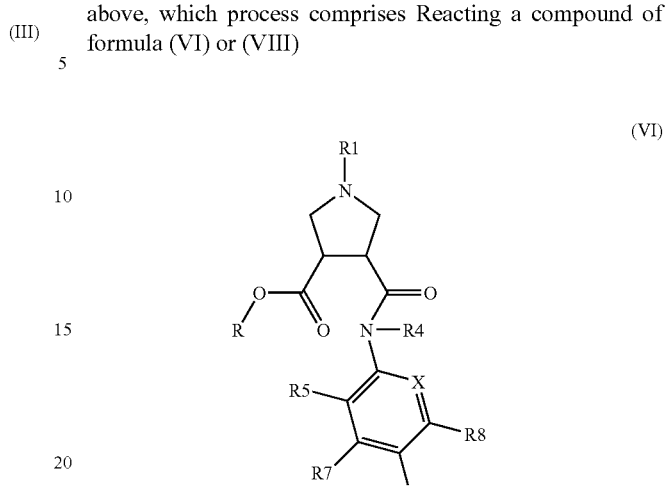

with a compound of formula (VII) or (V), respectively:

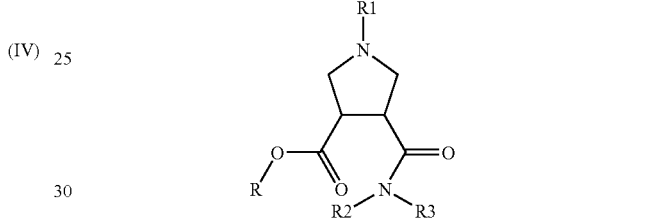

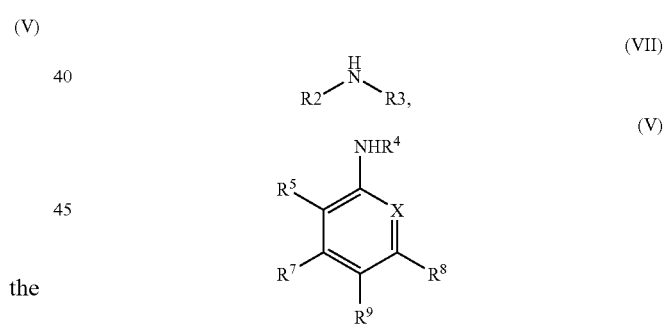

wherein $R^1$, $R^2$, $R^3$, $R^4$, $R^5$, $R^7$, $R^8$, $R^9$, and X have the significances given above, LG is a leaving group and R is lower alkyl, cycloalkyl or cycloalkyl-lower alkyl.

Suitable reaction conditions for the reaction of a compound of formula (VI) with a compound NHR²R³ are well known to the person skilled in the art. Such reactions can be carried out in a solvent such as e.g. DMF, acetonitrile, THF, toluene, heptane, and in the presence of a strong base like trialkyl alumina, NaH, LiHMDS, KHMDS at a suitable temperature, which can e.g. be chosen in the range of −10° C.-120° C.

In all general reaction descriptions the saponification process can be also avoided. Reactions from the ester to the corresponding amides are also possible in each reaction sequence 2c) throughout 2f).

General Synthetic Processes

Synthesis of pyrrolidine-3,4-dicarboxylic acid Scaffolds

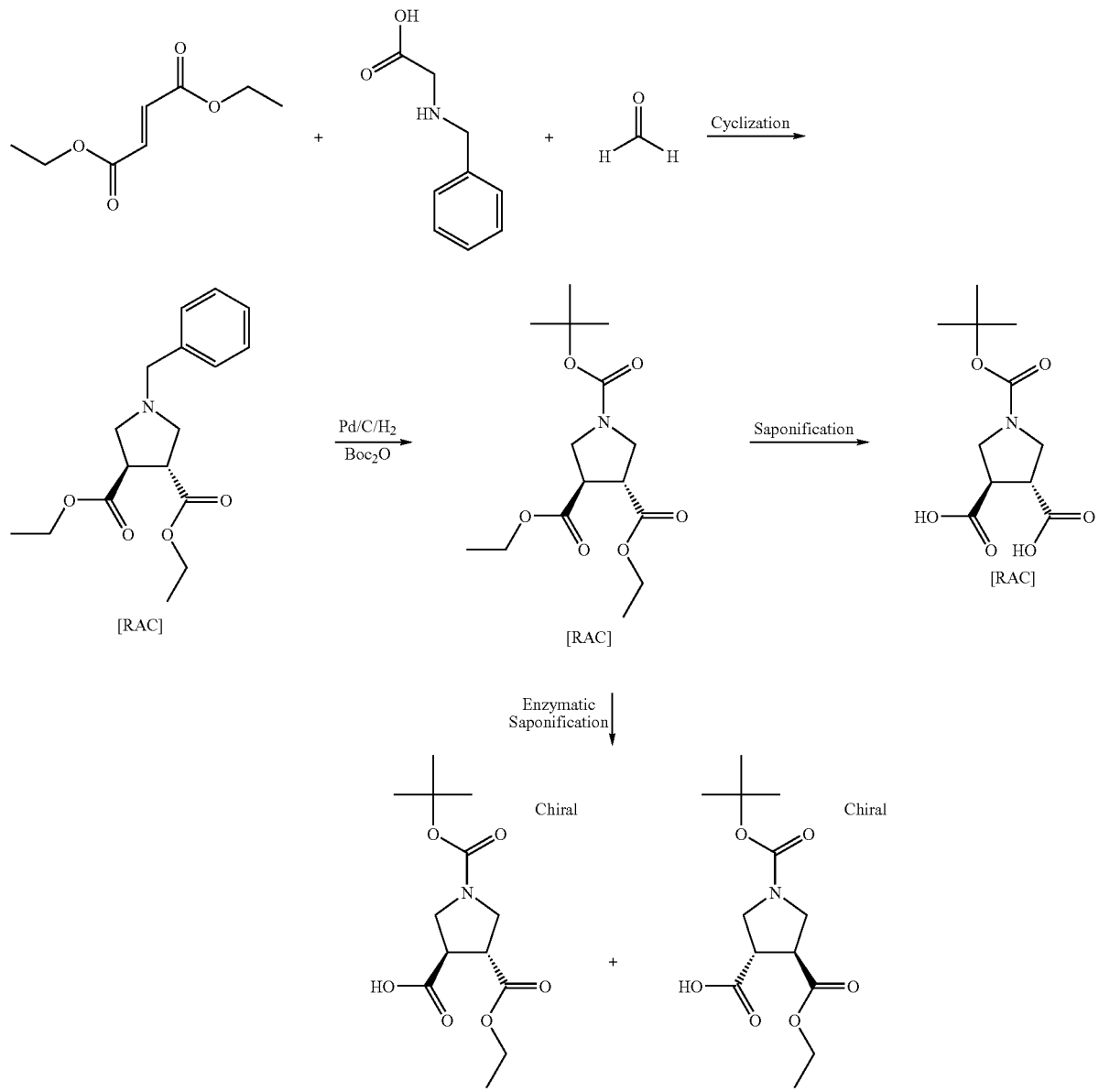

General Procedure:

An N-protected glycine derivative such as e.g. N-benzyl glycine is condensed with a source for formaldehyde like paraformaldehyde in a suitable solvent like benzene, toluene, xylene, DMF, DMA, DMSO or acetonitrile at elevated temperatures between 60-150° C. to the corresponding azomethine ylide. This species undergoes cycloaddition reactions with a suitable ester of fumaric acid like the corresponding diethyl ester or dimethyl ester in a one-pot procedure to yield the corresponding N-protected trans racemic mixture of pyrrolidine-3,4-dicarboxylic acid diesters. The N-protecting group is changed to the corresponding Boc- or Z-protecting group via cleavage of the first N-protecting group via e.g. catalytical hydrogenation. For this the protected pyrrolidine is dissolved in a suitable solvent like methanol, ethanol, THF or ethyl acetate followed by addition of a catalyst like Pd/C (e.g. 10%) to the mixture. After that a hydrogen atmosphere is generated to cleave the first N-protecting group. The free amine is then again protected by addition of $Boc_2O$ or Z-Cl, respectively.

The last step is the complete saponification of the diester to the corresponding diacid. The pyrrolidine diester is dissolved in suitable solvent system like methanol, ethanol, THF, 1,4-dioxane, water or mixtures thereof and a base like LiOH, NaOH, KOH, $Na_2CO_3$, $K_2CO_3$ or $Cs_2CO_3$ is added. Monohydrolysis can be performed using enantioselective enzymes or chiral bases in suitable solvents already described or in buffered aqueous systems.

Modifactions of Pyrrolidine Scaffolds:
Starting from N-Boc-pyrrolidine-3,4-dicarboxylic acids, introduction of $R^2$—NH—$R^3$

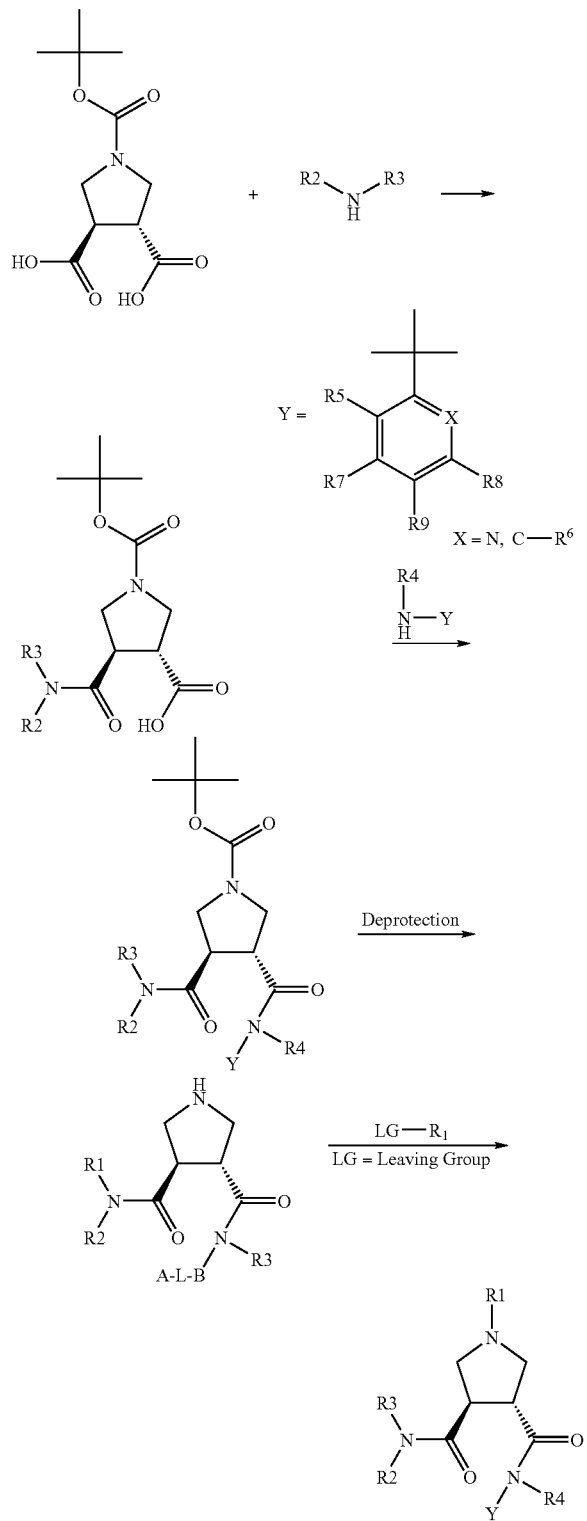

General Procedure:
N-protected pyrrolidine-3,4-dicarboxylic acid is dissolved in a suitable solvent like dichloromethane, DMF, acetonitrile, THF, NMP, DMA, etc. and activated with an amide coupling reagent like EDC, DIC, DCC, CDI, TBTU, HBTU, EEDQ, CIP, HOBt, HATU, PyBOP, PyBrOP, BOP, BOP-CL, TFFH, etc. at −10° C.-120° C. By adding one to two equivalents of the amine $R^2$—NH—$R^3$ the corresponding monoamide is obtained after reaction for 0.5-120 h at −10° C. to 120° C. Repetition of this reaction by using the same coupling reagents as mentioned above or transformation of the acid into the corresponding acid chloride or anhydride by means of oxalyl chloride, thionylchloride, isobutylcarbamoyl chloride or related reagents, with $R^4$—NH—Y yields the corresponding diamide.

After deprotection under standard conditions like treatment with acids (e.g. HCl, trifluoroacetic acid, HBr in glacial acetic acid) or hydrogenation in the case of the Z-protecting group the unprotected pyrrolidine-1,3-dicarboxamide is reacted with suitable reagents to introduce $R^1$. Suitable reagents LG-$R^1$ include alkylhalogenides (chlorides, bromides, iodides), -triflates, -para-nitrophenolates, -mesylates, acidchlorides, sulfonic acid chlorides, carbamoylchlorides, sulfamides, sulfamidoylchlorides, aldehydes, ketones etc. and can be reacted in solvents like dichloromethane, THF, acetonitrile, DMF, DMA, DMSO, NMP etc. with bases like DIEA, triethylamine, pyridine, N-methylmorpholine, $Na_2CO_3$, $K_2CO_3$, $Cs_2CO_3$ etc.

Starting from N-Boc-pyrrolidine-3,4-dicarboxylic acids, introduction of $R^4$—NH—Y

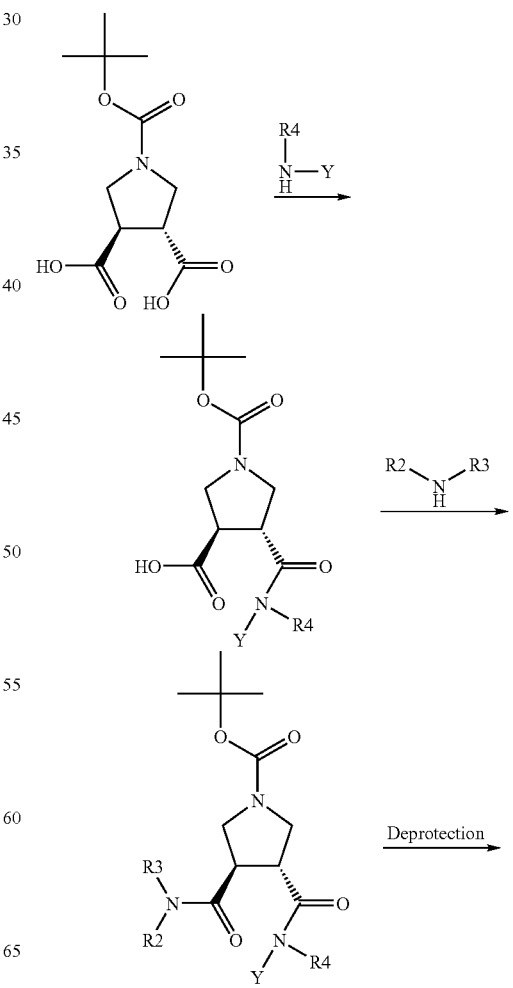

-continued

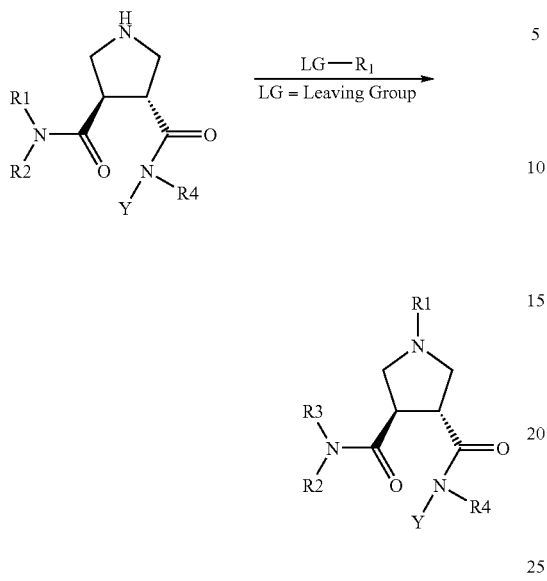

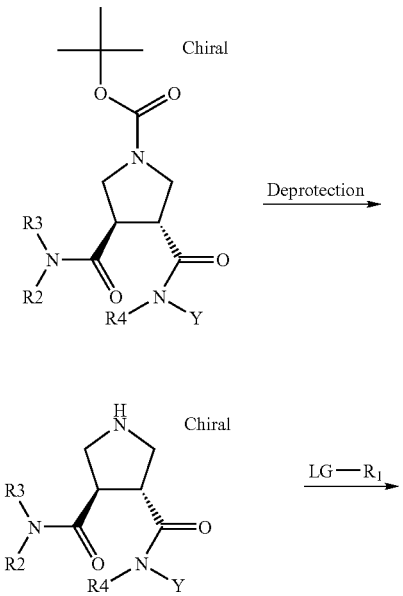

General Procedure:

Like 2a) with a different order of the reaction sequence.

Starting from R,R—N-Boc-pyrrolidine-3,4-dicarboxylic acid-3-ethylester, introduction of R²—NH—R³

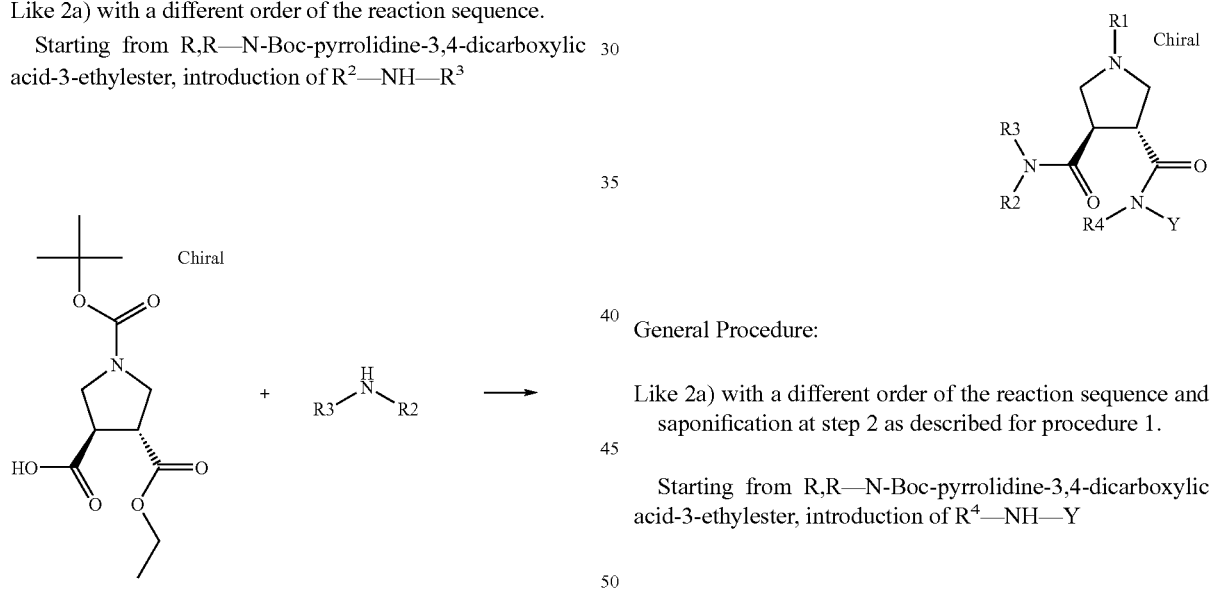

General Procedure:

Like 2a) with a different order of the reaction sequence and saponification at step 2 as described for procedure 1.

Starting from R,R—N-Boc-pyrrolidine-3,4-dicarboxylic acid-3-ethylester, introduction of R⁴—NH—Y

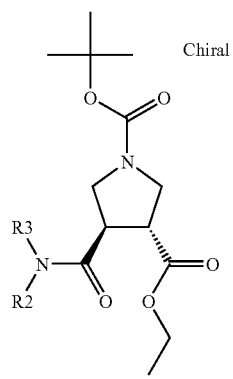

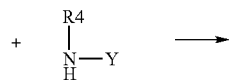

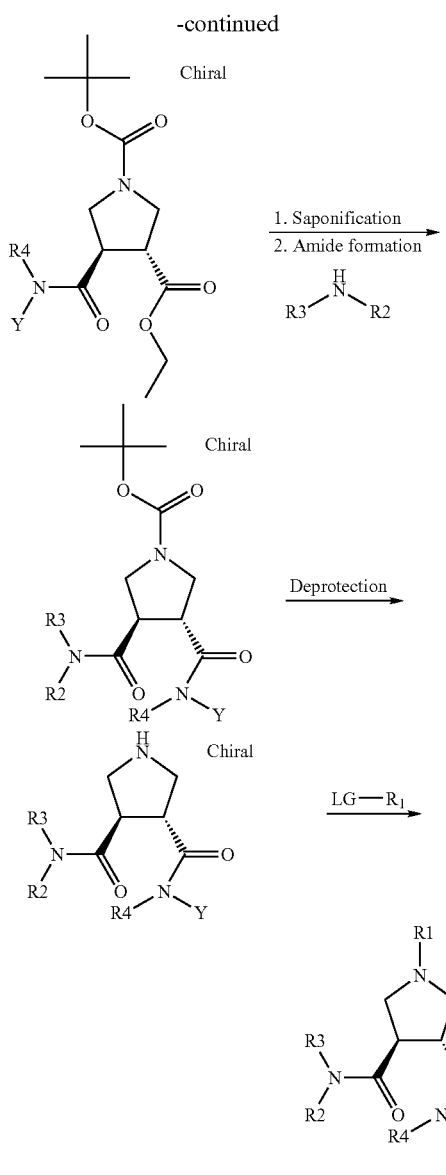
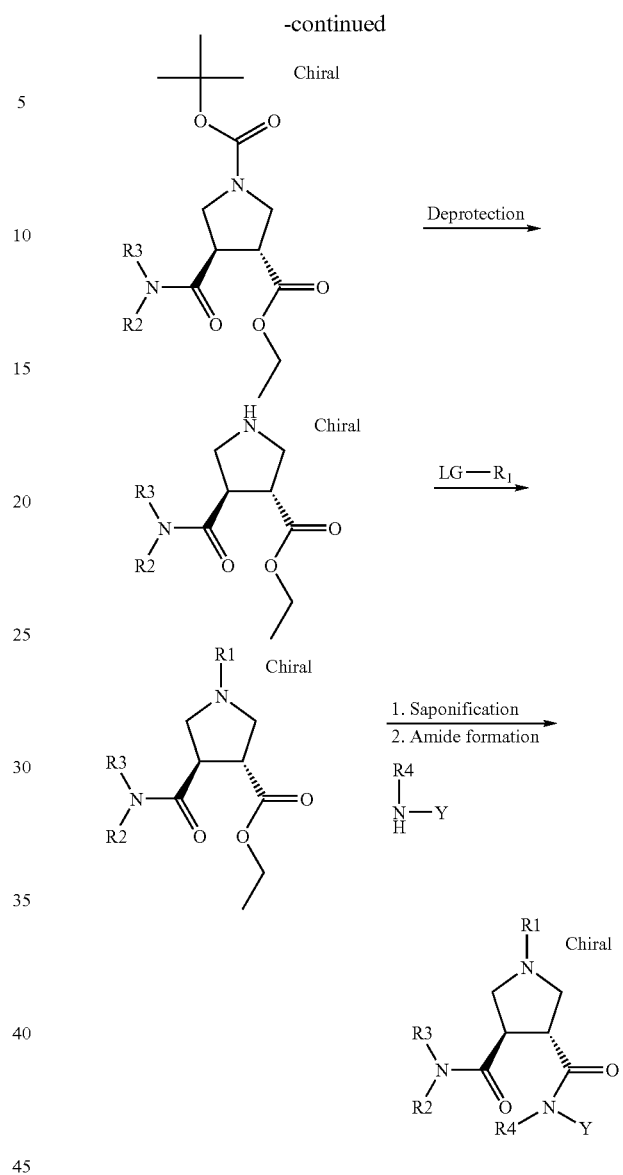
General Procedure:
Like 2c) with a different order of the reaction sequence.
Starting from R,R—N-Boc-pyrrolidine-3,4-dicarboxylic acid-3-ethylester, introduction of $R^2$—NH—$R^3$ and $R^1$
General Procedure:
Like 2c) with a different order of the reaction sequence.
Starting from R,R—N-Boc-pyrrolidine-3,4-dicarboxylic acid-3-ethylester, introduction of $R^4$—NH—Y and $R^1$
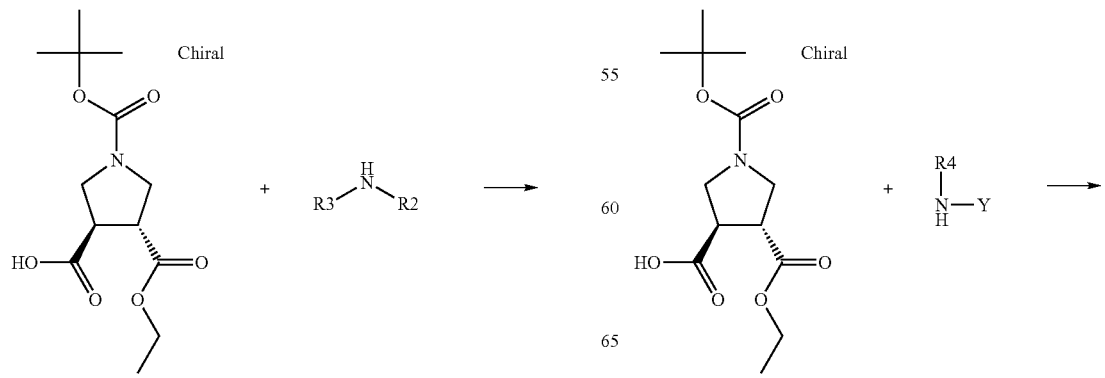

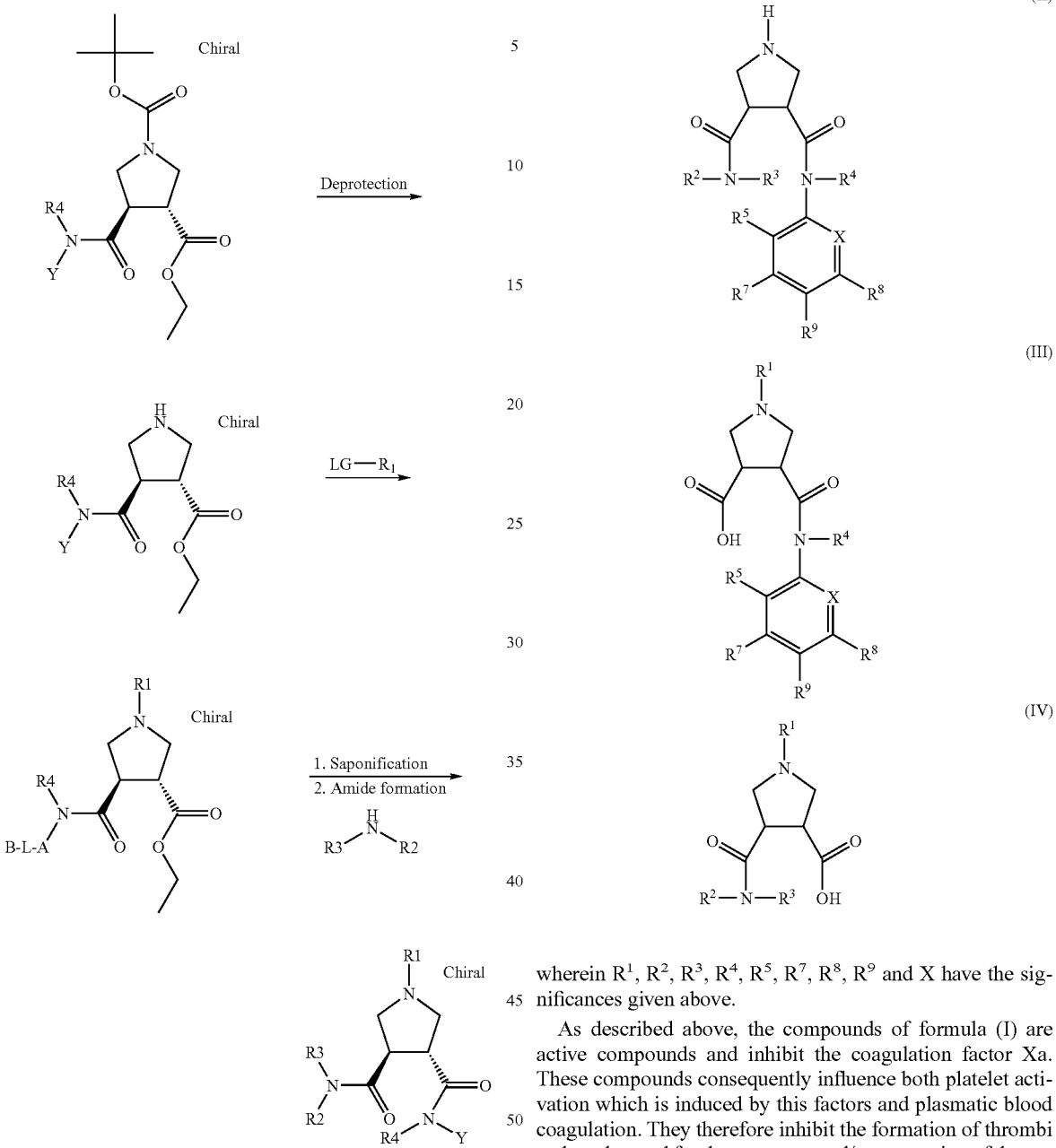

General Procedure:
Like 2c) with a different order of the reaction sequence.

Analogous reactions can be performed with the corresponding S,S enatiomers.

Insofar as their preparation is not described in the examples, the compounds of formula (I) as well as all intermediate products can be prepared according to analogous methods or according to the methods set forth above. Starting materials are commercially available or known in the art.

Furthermore, the invention relates to compounds of formula (I) as defined above, when manufactured by a process as described above. In another embodiment, the invention relates to the intermediates, the compounds of formula (II), (III) or (IV)

wherein $R^1$, $R^2$, $R^3$, $R^4$, $R^5$, $R^7$, $R^8$, $R^9$ and X have the significances given above.

As described above, the compounds of formula (I) are active compounds and inhibit the coagulation factor Xa. These compounds consequently influence both platelet activation which is induced by this factors and plasmatic blood coagulation. They therefore inhibit the formation of thrombi and can be used for the treatment and/or prevention of thrombotic disorders, such as, amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. The compounds of the present invention can also be used in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumour agents.

Prevention and/or treatment of thrombotic disorders, particularly arterial or deep vein thrombosis, is the preferred indication.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are associated with the coagulation factor Xa, particularly as therapeutically active substances for the treatment and/or prophylaxis of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour.

In another preferred embodiment, the invention relates to a method for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour, which method comprises administering a compound as defined above to a human being or animal.

The invention also embraces the use of compounds as defined above for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour.

The invention also relates to the use of compounds as described above for the preparation of medicaments for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour. Such medicaments comprise a compound as described above. The inhibition of the coagulation factor Xa by the compounds of the present invention can be demonstrated with the aid of a chromogenic peptide substrate assay as described hereinafter.

Factor Xa activity was measured spectrophotometrically in microtiter plates in a final volume of 150 µl using the following conditions: Inhibition of human factor Xa (Enzyme Research Laboratories) was tested at an enzyme concentration of 3 nM using the chromogenic substrate S-2222 (Chromogenix AB, Mölndal, Sweden) at 200 nM. The reaction kinetics of the enzyme and the substrate were linear with both time and the enzyme concentration. The inhibitors were dissolved in DMSO and tested at various concentrations up to 100 µM. The inhibitors were diluted using HNPT buffer consisting of HEPES 100 mM, NaCl 140 mM, PEG 6000 0.1% and Tween 80 0.02%, pH 7.8. The cleavage of S-2222 by human factor Xa was followed at 405 nm for 5 minutes at room temperature. The velocity of the reaction was determined by the autoreader from the slope of the linear regression fit to 7 time points (1 minute). The initial velocity for each inhibitor concentration was determined by the slope of at least 4 time points in the linear phase by a linear regression fit (mOD/min$^2$). Apparent dissociation constants $K_i$ were calculated according to Cheng and Prusoff [Cheng, Y. C.; Prusoff, W. H. Relationship between the inhibition constant ($K_i$) and the concentration of the inhibitor that causes 50 percent inhibition ($IC_{50}$) of an enzyme reaction. Biochem. Pharmacol. 1973, 22, 3099-3108.] based on the $IC_{50}$ and the respective $K_m$, determined previously ($K_i=IC_{50}/(1+S/K_m)$). The $K_m$ for the substrate used was determined under the conditions of the test with at least 5 substrate concentrations ranging from 0.5 to 15 times $K_m$. [Lottenberg R, Hall J A, Blinder M, Binder E P, Jackson C M., The action of thrombin on peptide p-nitroanilide substrates. Substrate selectivity and examination of hydrolysis under different reaction conditions. Biochim Biophys Acta. 1983 Feb. 15; 742(3):539-57]. according to Eadie [Eadie G. S. The inhibition of cholinesterase by physostigmine and prostigmine. J. Biol. Chem. 1942, 146, 85-93.]. The $K_m$ for S-2222 amounted to 613 µM.

The activity of the low molecular weight substances can, moreover, be characterized in the "prothrombin time" (PT) clotting test. The substances are prepared as a 10 mM solution in DMSO and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 µl of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 µl of plasma/inhibitor mixture in the measurement container. The clotting reaction was initiated by the addition of 0.1 ml of Dade® Innovin® (recombinant human tissue factor combined with calcium buffer and synthetic phospholipids, Dade Behring, Inc., Cat. B4212-50). The time up to the fibrin cross-linking was determined photooptically from the ACL. The inhibitor concentration, which brought about a doubling of the PT clotting time, was determined by fitting the data to an exponential regression (XLfit).

The compounds of the present invention can furthermore be characterised by the Activated Partial Thromboplastin time (aPTT). This coagulation test can e.g. be run on the ACL 300 Coagulation System (Instrumentation Laboratory) automatic analyzer. The substances are prepared as a 10 mM solution in DMSO and thereafter made up to the desired dilution in the same solvent. The test is performed with the Dade® Actin® FS Activated PTT reagent (purified soy phosphatides in 1.0×10$^{-4}$M ellagic acid, stabilizers and preservative, Dade Behring, Inc., Cat. B4218-100) Thereafter, 0.25 ml aliquots of human plasma (obtained from whole blood anticoagulated with 1/10 volume of 108 mM Na citrate) are spiked with 5 µl of test compound in at least 6 concentrations. 50 µl plasma at 4° C. containing 1/50 vol. inhibitor in solvent are incubated with 50 µl Dade® Actin® FS Activated PTT reagent in water at 37° C. for 3 min., then 50 µl CaCl2.2H2O 25 mM in water at 37° C. are added. The time up to the fibrin cross-linking was determined photooptically from the ACL. The inhibitor concentration, which brought about a doubling of the APTT dotting time, was determined by fitting the data to an exponential regression (XLfit).

The Ki values of the active compounds of the present invention preferably amount to about 0.001 to 50 μM, especially about 0.001 to 1 μM. The PT values preferably amount to about 1 to 100 μM, especially to about 1 to 10 μM. The aPTT values preferably amount to about 1 to 100 μM, especially to about 1 to 10 μM.

| Example | Ki [μM] factor Xa |
| --- | --- |
| 1 | 0.025 |
| 26 | 0.022 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Example 1 trans-(3RS,4RS)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}

According to the General Method 2a)

Step 1: trans-(3RS,4RS)-1-Benzyl-pyrrolidine-3,4-dicarboxylic acid diethyl ester 1a Fumaric acid diethylester (21.6 g; 0.126 mol) is dissolved in toluene (900 ml) and heated at 105° C. A mixture of N-benzylglycine (25 g; 0.151 mol) and paraformaldehyde (25.36 g; 0.844 mol) is added in 4 g portions to the refluxing solution. After completion of the addition the mixture is heated for 18 h at 105° C. The mixture is then evaporated to dryness and suspended in n-hexane. The insoluble material is filtered off and the remaining solution is evaporated to dryness. The crude product is used for the next step without further purification. Yield: 32.5 g (70.3%), ESI-MS: m/z=306 [M+H]$^+$ Step 2:
trans-(3RS,4RS)-Pyrrolidine-1,3,4-tricarboxylic acid tert-butyl ester diethyl ester 1b Under argon-atmosphere compound 1a (32.5 g; 0.106 mol) and di-tert.-butyldicarbonat (24.4 g; 0.112 mol) are dissolved in ethanol (650 ml). After that palladium on charcoal (10%; 3.4 g; 0.0034 mol) is added under argon-atmosphere and the argon-atmosphere is changed to hydrogen-atmosphere. After 2 h at 25° C. the hydrogenation is completed and palladium on charcoal is filtered off. The filtrate is evaporated to dryness and the residue is purified with flash chromatography over silica gel (700 g) using n-heptane/ethyl acetate (2:1) as eluent. Yield: 25.4 g (75.7%), ESI-MS: m/z=316 [M+H]$^+$ Step 3:
trans-(3RS,4RS)-Pyrrolidine-1,3,4-tricarboxylic acid tert-butyl ester 1c Compound 1b (1 g, 3.17 mmol) was dissolved in of THF (8 ml), and 80 mL of water was added. The reaction mixture was immersed in an ice-water bath and cooled to 0 C. To this reaction mixture, 96 ml of 0.25 N NaOH was added in small portions with stirring until the consumption of the starting diester was detected by thin-layer chromatography. The reaction was stirred at the same temperature for about 30 min to 1 h, and the reaction mixture was acidified with 1 N HCl at 0° C., saturated with NaCl, extracted with ethyl acetate four times (each 100 ml), and dried with sodium sulfate. The organic phase is evaporated to dryness and dried in vacuo. Yield: 0.68 g (82.7%), ESI-MS: m/z=258 [M–H]⁻

Step 4: trans-(3RS,4RS)-4-(4-Chlorophenylcarbamoyl)-pyrrolidine-1,3-dicarboxylic acid 1-tert-butyl ester 1d Compound 1c (2.25 g; 9 mmol) is suspended in acetonitrile (30 ml) and N,N-diisopropyl ethyl amin (3.03 ml; 17 mmol) is added at 25° C. After 20 min a clear solution is obtained and 1-(3-dimethylaminopropyl)-3-ethylcarbodiimide hydrochloride EDCI (2.0 g; 10 mmol) and 1-hydroxybenzotriazole HOBt (1.41 g; 10 mmol) is added. After stirring for 30 min at 25° C. 4-chloroaniline (1.11 g; 9 mmol) is added to the reaction mixture. The mixture is stirred for 18 h at 25° C., evaporated to dryness and dissolved in ethyl acetate (100 ml). The organic phase is washed with 0.1 N HCl (2×100 ml), water and brine and dried over Na2SO4. The organic phase is filtered and the filtrate is evaporated to dryness. Yield: 1.08 g (33.7%), ESI-MS: m/z=368 [M–H]⁻, Cl-pattern Step 5: 1-(4-Amino-3-fluoro-phenyl)-1H-pyridin-2-one 1e 4-Bromo-2-fluoroaniline (13.0 g; 68 mmol), 2-hydroxypyridine (9.11 g; 96 mmol), 8-hydroxyquinoline (1.5 g; 10 mmol) are dissolved under argon in DMSO (40 ml). To this solution K$_2$CO$_3$ (10.4 g; 75 mmol) and CuI (1.95 g; 10 mmol) are added and the resulting suspension is heavily stirred under argon at 150° C. for 18 h. The mixture is evaporated to dryness under reduced pressure and the final residue is chromatographed over silica gel (400 g) using dichloromethane/methanol as eluents. The obtained crude product is recrystallized with diethyl ether to yield an off-white solid. Yield: 2.80 g (20.0%), ESI-MS: m/z=205 [M+H]⁺

Step 6: trans-(3RS,4RS)-Pyrrolidine-3,4-dicarboxylic acid 3-[(4-chloro-phenyl)-amide] 4-{[2-fluoro-4-(2-oxo-2H-pyridin-1-yl)-phenyl]-amide} hydrochloride 1f Compound 1d (0.8 g; 2 mmol) is dissolved in thionylchloride (3.93 ml; 54 mmol), after 30 min stirring at 25° C. 1-(4-amino-3-fluoro-phenyl)-1H-pyridin-2-one (compound 1e, 0.443 g; 2 mmol) is added under cooling. The mixture is stirred for 18 h at 25° C., evaporated to dryness and recrystallized from diethyl ether yielding compound 1f as light brown solid as hydrochloride. Yield: 0.872 g (81.8%), ESI-MS: m/z=455 [M+H]⁺, Cl-pattern Step 7: trans-(3RS,4RS)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide} 1 g Compound 1f (80.3 mg; 0.177 mmol) is dissolved in acetonitrile (3 ml) under addition of N,N-diisopropyl ethyl amine (45.75 mg; 61.8 µl; 0.354 mmol). Methanesulfonylchloride (40.6 mg; 0.354 mmol) is added and the mixture is stirred for 18 h at 25° C. The reaction mixture is evaporated to dryness and purified with preparative HPLC chromatography. Yield: 11.2 mg (11.9%), ESI-MS: m/z=533 [M+H]⁺, Cl-pattern Example 2 trans-(3RS,4RS)-1-Formyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 2 was prepared as described for example 1 with the exception of step 7

Step 7: trans-(3RS,4RS)-1-Formyl-pyrrolidine-3,4-dicarboxylic acid 3-[(4-chloro-phenyl)-amide] 4-{[2-fluoro-4-(2-oxo-2H-pyridin-1-yl)-phenyl]-amide} 2

Compound 1f (80.3 mg; 0.177 mmol) is dissolved in acetonitrile (3 ml) under addition of N,N-diisopropyl ethyl amine (22.9 mg; 30.9 µl; 0.177 mmol). 4-Nitrophenylformiate (29.6 mg; 0.177 mmol) is added and the mixture is stirred for 18 h at 25° C. The reaction mixture is evaporated to dryness and purified with preparative HPLC chromatography. Yield: 13.8 mg (16.1%), ESI-MS: m/z=483 [M+H]⁺, Cl-pattern Example 3 trans-(3RS,4RS)-{3-(4-Chloro-phenylcarbamoyl)-4-[2-fluoro-4-(2-oxo-2H-pyridin-1-yl)-phenylcarbamoyl]-pyrrolidin-1-yl}-acetic acid ethyl ester The compound of example 3 was prepared as described for example 1 with the exception of step 7

Step 7: trans-(3RS,4RS)-{3-(4-Chloro-phenylcarbamoyl)-4-[2-fluoro-4-(2-oxo-2H-pyridin-1-yl)-phenylcarbamoyl]-pyrrolidin-1-yl}-acetic acid ethyl ester 3

Compound 1f (80.3 mg; 0.177 mmol) and K$_2$CO$_3$ (69.0 mg; 0.5 mmol) are suspended in acetonitrile (3 ml). After that bromo acetic acid ethyl ester (32.5 mg; 0.195 mmol) is added and the mixture is stirred for 18 h at 25° C. The reaction mixture is evaporated to dryness and purified with preparative HPLC chromatography. Yield: 18.8 mg (19.6%), ESI-MS: m/z=541 [M+H]⁺, Cl-pattern.

Example 4 trans-(3RS,4RS)-1-Carbamoylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 4 was prepared as described for example 1 with the exception of step 7

Step 7: trans-(3RS,4RS)-1-Carbamoylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide} 4

Compound 1f (80.3 mg; 0.177 mmol) and K$_2$CO$_3$ (69.0 mg; 0.5 mmol) are suspended in acetonitrile (3 ml). After that 2-bromo-acetamide (27.0 mg; 0.195 mmol) is added and the mixture is stirred for 18 h at 25° C. The reaction mixture is evaporated to dryness and purified with preparative HPLC chromatography. Yield: 10.8 mg (11.9%), ESI-MS: m/z=512 [M+H]⁺, Cl-pattern

Example 5 trans-(3RS,4RS)-1-Cyanomethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 5 was prepared as described for example 1 with the exception of step 7

Step 7: trans-(3RS,4RS)-1-Cyanomethyl-pyrrolidine-3,4-dicarboxylic acid 3-[(4-chloro-phenyl)-amide] 4-{[2-fluoro-4-(2-oxo-2H-pyridin-1-yl)-phenyl]-amide} 5

Compound 1f (80.3 mg; 0.177 mmol) and $K_2CO_3$ (69.0 mg; 0.5 mmol) are suspended in acetonitrile (3 ml). After that 2-bromo-acetonitrile (23.4 mg; 0.195 mmol) is added and the mixture is stirred for 18 h at 25° C. The reaction mixture is evaporated to dryness and purified with preparative HPLC chromatography. Yield: 10.4 mg (11.9%), ESI-MS: m/z=494 $[M+H]^+$, Cl-pattern

Example 6 trans-(3RS,4RS)-1-(3,3,3-Trifluoro-propyl)-pyrrolidine-3,4-dicarboxylic acid 3-[(4-chloro-phenyl)-amide]-4-{[2-fluoro-4-(2-oxo-2H-pyridin-1-yl)-phenyl]-amide}

The compound of example 6 was prepared as described for example 1 with the exception of step 7

Step 7: trans-(3RS,4RS)-1-(3,3,3-Trifluoro-propyl)-pyrrolidine-3,4-dicarboxylic acid 3-[(4-chloro-phenyl)-amide]-4-{[2-fluoro-4-(2-oxo-2H-pyridin-1-yl)-phenyl]-amide} 6

Compound 1f (80.3 mg; 0.177 mmol) and $K_2CO_3$ (69.0 mg; 0.5 mmol) are suspended in acetonitrile (3 ml). After that 3-bromo-1,1,1-trifluoropropane (34.5 mg; 0.195 mmol) and $Ag_2O$ (45.2 mg; 0.195 mmol) is added and the mixture is stirred for 18 h at 80° C. The reaction mixture is evaporated to dryness and purified with preparative HPLC chromatography. Yield: 19.7 mg (20.2%), ESI-MS: m/z=551 $[M+H]^+$, Cl-pattern

Example 7

(3R,4R)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}

According to General Method 2c)

Step 1: (3R,4R)-Pyrrolidine-1,3,4-tricarboxylic acid-1-tert-butyl ester-3-ethyl ester 7a The stereoselective mono saponification of the racemic mixture of compound 1b to compound 7a and the corresponding S,S-enantiomer is described in: R. M. Rodriguez Sarmiento, B. Wirz, H. Iding, Tetrahedron Asymmetry, 14, 2003, 1547-1551.

Step 2a: (3R,4R)-4-(4-Chlorophenylcarbamoyl)-pyrrolidine-1,3-dicarboxylic acid 1-tert-butyl ester-3-ethyl ester 7b Compound 7a (4.91 g; 17.1 mmol) is suspended in acetonitrile (25 ml) and N,N-diisopropyl ethyl amin (3.58 ml; 20.5 mmol) is added at 0° C. Bis(2-oxo-3-oxazolidinyl) phosphinic chloride BOP-Cl (5.22 g; 20.5 mmol) is added as a solid and after stirring for 30 min at 0° C. 4-chloroaniline (2.18 g; 17.1 mmol) is added to the reaction mixture. The mixture is stirred for 2 h at 0° C., evaporated to dryness and dissolved in ethyl acetate (ml). The organic phase is washed with 0.1 N HCl (2×ml), with saturated aquous $Na_2CO_3$ solution, water and brine and dried over $Na_2SO_4$. The organic phase is filtered and the filtrate is evaporated to dryness. The crude product is purified by silica gel chromatography. Yield: 4.7 g (69.3%), ESI-MS: m/z=395 $[M-H]^-$, Cl-pattern Step 2b: (3R,4R)-4-(4-Chlorophenylcarbamoyl)-pyrrolidine-1,3-dicarboxylic acid 1-tert-butyl ester 7c The ester obtained from step 2a (4.07 g; 10.3 mmol) is dissolved in a mixture of THF/water (1:1; 40 ml). LiOH monohydrate (0.947 g; 22.6 mmol) is added to the mixture and complete saponification is obtained after stirring for 18 h at 25° C. The mixture is acidified with 1N aq. HCl and diluted with ethyl acetate (100 ml). The organic phase is washed with brine (100 ml) and dried over $Na_2SO_4$. The organic phase is filtered and the filtrate is evaporated to dryness. Yield: 3.28 g (86.7%), ESI-MS: m/z=367 $[M-H]^-$, Cl-pattern Step 3: (3R,4R)-Pyrrolidine-3,4-dicarboxylic acid 3-[(4-chloro-phenyl)-amide] 4-{[2-fluoro-4-(2-oxo-2H-pyridin-1-yl)-phenyl]-amide} hydrochloride 7d Compound 7c (2.2 g; 5.96 mmol) is dissolved in thionylchloride (10 ml) and stirred at 25° C. for 30 min. After that 1-(4-amino-3-fluoro-phenyl)-1H-pyridin-2-one (compound 1e; 1.22 g; 5.96 mmol) is added and the reaction mixture is stirred for 18 h at ambient temperature. The mixture is evaporated to dryness and the crude product is recrystallized from diethylether several times to yield compound 7d as light brown solid. Yield: 2.92 g (99.7%), ESI-MS: m/z=455 $[M+H]^+$, Cl-pattern Step 4: (3R,4R)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide} 7e Compound 7d (300 mg; 0.61 mmol) is dissolved in acetonitrile (5 ml) under addition of N,N-diisopropyl ethyl amine (210 µl; 1.22 mmol). Methanesulfonylchloride (140 mg; 1.22 mmol) is added and the mixture is stirred for 18 h at 25° C. The reaction mixture is evaporated to dryness and purified with preparative HPLC. Yield: 170 mg (5.22%), ESI-MS: m/z=533 $[M+H]^+$, Cl-pattern

Example 8

(3R,4R)-1-Ethanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 8 was prepared according to the methods described for example 7. ESI-MS: m/z=547 $[M+H]^+$, Cl-pattern

Example 9

(3R,4R)-1-Propanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 9 was prepared according to the methods described for example 7. ESI-MS: m/z 561 [M+H]$^+$, Cl-pattern

Example 10

(3R,4R)-1-(Propane-2-sulfonyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 10 was prepared according to the methods described for example 7. ESI-MS: m/z=561 [M+H]$^+$, Cl-pattern

Example 11

(3R,4R)-1-(2,2,2-Trifluoro-ethanesulfonyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 11 was prepared according to the methods described for example 7. ESI-MS: m/z=601 [M+H]$^+$, Cl-pattern

Example 12

(3R,4R)-1-Dimethylsulfamoyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of Example 12 was prepared according to the methods described for example 7. ESI-MS: m/z=562 [M+H]$^+$, Cl-pattern

Example 13

(3R,4R)-1-Acetyl-pyrrolidine-3,4-dicarboxylic acid 3-[(4-chloro-phenyl)-amide] 4-{[2-fluoro-4-(2-oxo-2H-pyridin-1-yl)-pbenyl]-amide}

The compound of Example 13 was prepared according to the methods described for example 7. ESI-MS: m/z=497 [M+H]$^+$, Cl-pattern

Example 14

(3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid methyl ester The compound of example 14 was prepared according to the methods described for example 7. ESI-MS: m/z=513 [M+H]$^+$, Cl-pattern

Example 15

(3R,4R)-1-(2-Fluoro-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 15 was prepared according to the methods described for example 7 with the exception of step 4.

Step 4:

Compound 7d (100 mg; 0.2 mmol) is dissolved in acetonitrile (2 ml) under addition K$_2$CO$_3$ (56 mg; 0.4 mmol). 2-Fluoroethylbromide (59 mg; 0.41 mmol) and Ag$_2$O (47 mg; 0.2 mmol) is added to the reaction mixture. The mixture is stirred at 80° C. until a full conversion to example 23 is observed. The reaction mixture is evaporated to dryness and purified with preparative HPLC. Yield: 20 mg (18.9%), ESI-MS: m/z=501 [M+H]$^+$, Cl-pattern

Example 16

(3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid ethyl ester The compound of example 16 was prepared according to the methods described for example 7. ESI-MS: m/z=527 [M+H]$^+$, Cl-pattern

Example 17

(3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid propyl ester The compound of example 17 was prepared according to the methods described for example 7. ESI-MS: m/z=541 [M+H]$^+$, Cl-pattern

Example 18

(3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid isopropyl ester The compound of example 18 was prepared according to the methods described for example 7. ESI-MS: m/z=541 [M+H]$^+$, Cl-pattern

Example 19

(3R,4R)-1-(Pyrrolidine-1-carbonyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 19 was prepared according to the methods described for example 7. ESI-MS: m/z=552 [M+H]$^+$, Cl-pattern

Example 20

(3S,4S)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 20 was prepared according to the methods described for example 7 starting from the (3S, 4S)-enantiomer. ESI-MS: m/z=533 [M+H]$^+$, Cl-pattern

Example 21

(3R,4R)-1-Sulfamoyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 21 was prepared according to the methods described for example 7 with the exception of step 4.

Step 4:

Compound 7d (100 mg; 0.2 mmol) is dissolved in diglyme (1 ml). The mixture is heated at 160° C. and a solution of sulfamide (23 mg; 0.24 mmol) in diglyme (1 ml) is dropped to the reaction mixture within 5 min. The reaction mixture is heated at 160° C. until a full conversion to example 21 is observed. The reaction mixture is evaporated to dryness and purified with preparative HPLC. Yield: 4 mg (3.7%), ESI-MS: m/z=534 [M+H]$^+$, Cl-pattern

Example 22

(3R,4R)-1-Formylpyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 22 was prepared according to the methods described for example 7 with the exception of step 4.

Step 4:

Compound 7d (100 mg; 0.2 mmol) is dissolved in acetonitrile (2 ml) under addition of N,N-diisopropyl ethyl amine (30 µl; 0.2 mmol). Formic acid-4-nitrophenyl ester (34 mg; 0.2 mmol) is added to the reaction mixture. The mixture is stirred at ambient temperature until a full conversion to example 22 is observed. The reaction mixture is evaporated to dryness and purified with preparative HPLC. Yield: 40.4 mg (41.1%), ESI-MS: m/z=483 [M+H]$^+$, Cl-pattern

Example 23

(3R,4R)-1-(2,2,2-Trifluoro-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 23 was prepared according to the methods described for example 7 with the exception of step 4.

Step 4:

Compound 7d (80 mg; 0.16 mmol) is dissolved in dichloromethane (2 ml) under addition of N,N-diisopropyl ethyl amine (60 µl; 0.41 mmol). 2,2,2-Trifluoroethyltriflate (57 mg; 0.24 mmol) is added to the reaction mixture. The mixture is stirred at ambient temperature until a full conversion to example 23 is observed. The reaction mixture is evaporated to dryness and purified with preparative HPLC. Yield: 10.0 mg (11.4%), ESI-MS: m/z=537 [M+H]$^+$, Cl-pattern

Example 24

(3R,4R)-1-(2,2-Difluoro-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 24 was prepared according to the methods described for example 7 with the exception of step 4.

Step 4:

Compound 7d (100 mg; 0.2 mmol) is dissolved in acetonitrile (2 ml) under addition K$_2$CO$_3$ (56 mg; 0.4 mmol). 2,2-Difluoroethylbromide (59 mg; 0.41 mmol) and Ag$_2$O (47 mg; 0.2 mmol) is added to the reaction mixture. The mixture is stirred at 80° C. until a full conversion to example 23 is observed. The reaction mixture is evaporated to dryness and purified with preparative HPLC. Yield: 20 mg (18.9%), ESI-MS: m/z=519 [M+H]$^+$, Cl-pattern

Example 25

(3R,4R)-1-(2-Hydroxy-ethyl)-pyrrolidine-3,4-dicarboxylic acid 3-[(4-chloro-phenyl)-amide] 4-{[2-fluoro-4-(2-oxo-2H-pyridii-1-yl)-phenyl]-amide}

The compound of example 25 was prepared according to the methods described for example 24. ESI-MS: m/z=500 [M+H]$^+$, Cl-pattern

Example 26

(3R,4R)-1-Methylcarbamoylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 26 was prepared according to the methods described for example 24. ESI-MS: m/z=526 [M+H]$^+$, Cl-pattern

Example 27

(3R,4R)-1-Isopropyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 27 was prepared according to the methods described for example 24 with the exception of step 4.

Step 4:

Compound 7d (100 mg; 0.2 mmol) is dissolved in a mixture of methanol and acetic acid (9:1; 2 ml). Aceton (24 mg; 0.41 mmol) is added and the reaction mixture is stirred for 30 min at 25° C. After that NaBH$_3$CN (45 mg; 0.71 mmol) is added to the mixture. After stirring for 18 h at ambient temperature the reaction mixture is treated once again with aceton (24 mg; 0.41 mmol) and NaBH$_3$CN (45 mg; 0.71 mmol) and stirred at 80° C. for 18 h. After that the mixture is evaporated to dryness and purified with preparative HPLC. Yield: 3 mg (3%), ESI-MS: m/z=497 [M+H]$^+$, Cl-pattern

Example 28

(3R,4R)-1-Methanesulfonyl-pyrrolidine-3,4-dicarboxylic acid 3-{[2-fluoro-4-(2-oxo-2H-pyridin-1-yl)-phenyl]-amide} 4-[(1H-indol-5-yl)-amide]

According to General Method 2d)

Step 1: (3R,4R)-Pyrrolidine-1,3,4-tricarboxylic acid-1-tert-butyl ester-3-ethyl ester 7a The stereoselective mono saponification of the racemic mixture of compound 1b to compound 7a and the corresponding S,S-enantiomer is described in: R. M. Rodriguez Sarmiento, B. Wirz, H. Iding, Tetrahedron Asymmetry, 14, 2003, 1547-1551.

Step 2: (3R,4R)-4-[2-Fluoro-4-(2-oxo-2H-pyridin-1-yl)-phenylcarbamoyl]-pyrrolidine-1,3-dicarboxylic acid 1-tert-butyl ester 3-ethyl ester 28b Compound 7a (1.85 g; 6 mmol) is suspended in acetonitrile (20 ml) and N,N-diisopropyl ethyl amin (1.65 ml; 10 mmol) is added at 25° C. BOP-CL (2.46 g; 10 mmol) is added as a solid and after stirring for 30 min at 25° C. 1-(4-amino-3-fluoro-phenyl)-1H-pyridin-2-one (1.45 g; 7 mmol) is added to the reaction mixture. The mixture is stirred for 4 d at 25° C., evaporated to dryness and dissolved in ethyl acetate (200 ml). The organic phase is washed with 2 N HCl (50 ml), with 10% aqueous $Na_2CO_3$ solution, water and brine and dried over $Na_2SO_4$. The organic phase is filtered and the filtrate is evaporated to dryness. The crude product is purified by silica gel chromatography. Yield: 1.77 g (58.1%), ESI-MS: m/z=472 [M−H]⁻

Step 3: (3R,4R)-4-[2-Fluoro-4-(2-oxo-2H-pyridin-1-yl)-phenylcarbamoyl]-pyrrolidine-3-carboxylic acid ethyl ester hydrochloride 28c Compound 28b (5.37 g; 11 mmol) is dissolved in 6 N HCl in isopropanol (42 ml) and the mixture is stirred for 2 h at 25° C. The mixture is evaporated to dryness and the crude product is recrystallized from diethylether several times to yield compound 28c as an off-white solid. Yield: 4.89 g (105.2%), ESI-MS: m/z=374 [M+H]⁺

Step 4: (3R,4R)-4-[2-Fluoro-4-(2-oxo-2H-pyridin-1-yl)-phenylcarbamoyl]-1-methane-sulfonyl-pyrrolidine-3-carboxylic acid ethyl ester 28d Compound 28c (3.1 g; 8 mmol) is suspended in acetonitrile (20 ml) under addition of N,N-diisopropyl ethyl amine (3.24 ml; 19 mmol). Methanesulfonylchloride (1.3 g; 11 mmol) is added and the mixture is stirred for 18 h at 25° C. The reaction mixture is evaporated to dryness and purified by silica gel chromatography. Yield: 3.5 g (102.5%), ESI-MS: m/z=450 [M−H]⁻

Step 5: (3R,4R)-4-[2-Fluoro-4-(2-oxo-2H-pyridin-1-yl)-phenylcarbamoyl]-1-methane-sulfonyl-pyrrolidine-3-carboxylic acid 28e Compound 28d (3.7 g; 8 mmol) is dissolved in a mixture of 1,4-dioxane/water (1:1; 30 ml). LiOH monohydrate (1.03 g; 25 mmol) is added to the mixture and complete saponification is obtained after stirring for 24 h at 25° C. The mixture is evaporated to dryness and dissolved in ethyl acetate and the product is extracted with saturated aqueous $Na_2CO_3$ solution. The aqueous phase is cooled to 10° C. and acidified with 25% aqueous HCl solution until pH=1. The product is extracted several times with ethylacetate (3×100 ml). The combined organic phases are washed with brine and dried over $Na_2SO_4$. After filtration the organic phase is evaporated to dryness. Yield: 1.57 g (45.2%), ESI-MS: m/z=422 [M−H]⁻

Step 6: (3R,4R)-1-Methanesulfonyl-pyrrolidine-3,4-dicarboxylic acid 3-{[2-fluoro-4-(2-oxo-2H-pyridin-1-yl)-phenyl]-amide} 4-[(1H-indol-5-yl)-amide] 28f Compound 28e (100 mg; 0.236 mmol) is suspended in acetonitrile (1 ml) and N,N-diisopropyl ethyl amin (60 µl; 0.354 mmol) is added at 25° C. BOP-Cl (90 mg; 0.354 mmol) is added as a solid and after stirring for 30 min at 25° C. 5-amino indole (34 mg; 0.286 mmol) is added to the reaction mixture. The mixture is stirred for 18 h at 25° C., evaporated to dryness and purified by silica gel chromatography. Yield: 88 mg (69.3%), ESI-MS: m/z=538 [M+H]⁺

Example 29

(3R,4R)-1-Methanesulfonyl-pyrrolidine-3,4-dicarboxylic acid 3-{[2-fluoro-4-(2-oxo-2H-pyridin-1-yl)-phenyl]-amide} 4-[(4-methoxy-phenyl)-amide]

The compound of example 29 was prepared according to the methods described for example 28. ESI-MS: m/z=529 [M+H]⁺

Example 30

(3R,4R)-1-Methanesulfonyl-pyrrolidine-3,4-dicarboxylic acid 3-[(3-chloro-4-methoxy-phenyl)-amide] 4-{[2-fluoro-4-(2-oxo-2H-pyridin-1-yl)-phenyl]-amide}

The compound of example 30 was prepared according to the methods described for example 28. ESI-MS: m/z=563 [M+H]⁺, Cl-Pattern

Example 31

(3R,4R)-1-Methanesulfonyl-pyrrolidine-3,4-dicarboxylic acid 3-[(3-fluoro-4-methoxy-phenyl)-amide] 4-{[2-fluoro-4-(2-oxo-2H-pyridin-1-yl)-phenyl]-amide}

The compound of example 31 was prepared according to the methods described for example 28. ESI-MS: m/z=547 [M+H]⁺

Example 32

(3R,4R)-1-Methanesulfonyl-pyrrolidine-3,4-dicarboxylic acid 3-[(4-chloro-3-fluoro-phenyl)-amide] 4-{[2-fluoro-4-(2-oxo-2H-pyridin-1-yl)-phenyl]-amide}

The compound of example 32 was prepared according to the methods described for example 28. ESI-MS: m/z=551 [M+H]⁺, Cl-Pattern

Example 33

(3R,4R)-1-Methanesulfonyl-pyrrolidine-3,4-dicarboxylic acid 3-[(4-chloro-2-fluoro-phenyl)-amide] 4-{[2-fluoro-4-(2-oxo-2H-pyridin-1-yl)-phenyl]-amide}

The compound of example 33 was prepared according to the methods described for example 28. ESI-MS: m/z=551 [M+H]⁺, Cl-Pattern

Example 34

(3R,4R)-1-Methanesulfonyl-pyrrolidine-3,4-dicarboxylic acid 3-[(2-amino-4-chloro-phenyl)-amide] 4-{[2-fluoro-4-(2-oxo-2H-pyridin-1-yl)-phenyl]-amide}

The compound of example 34 was prepared according to the methods described for example 28. ESI-MS: m/z=548 [M+H]⁺, Cl-Pattern

Example 35

(3R,4R)-1-Methanesulfonyl-pyrrolidine-3,4-dicarboxylic acid 3-[(4-chloro-phenyl)-methyl-amide] 4-{[2-fluoro-4-(2-oxo-2H-pyridin-1-yl)-phenyl]-amide}

The compound of example 35 was prepared according to the methods described for example 28. ESI-MS: m/z=547 [M+H]$^+$, Cl-Pattern

Example 36

(3R,4R)-1-Methanesulfonyl-pyrrolidine-3,4-dicarboxylic acid 3-{[2-fluoro-4-(2-oxo-2H-pyridin-1-yl)-phenyl]-amide} 4-[(1H-indazol-5-yl)-amide]

The compound of example 36 was prepared according to the methods described for example 28. ESI-MS: m/z=539 [M+H]$^+$

Example 37

(3R,4R)-1-Methanesulfonyl-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}

The compound of example 37 was prepared according to the methods described for example 28 with the exception of step 6.

Step 6

Compound 28e (35 mg; 0.083 mmol) is dissolved under argon in thionylchlorid (0.03 ml; 0.413 mmol) to generate the corresponding acidchlorid. The mixture is stirred for 30 min at 25° C. 2-Amino-chloro pyridine is dissolved in THF and NaH suspension in oil (55%; 24 mg; 0.58 mmol) is added under hydrogen evolution. The mixture is stirred for 30 min at 25° C. The corresponding acidchloride solution is added to the reaction mixture of the deprotonated 2-amino-chloro pyridine. The combined suspensions are stirred for 7 d at 25° C. The reaction suspension is evaporated to dryness and purified by silica gel chromatography. Yield: 36 mg (81.5%), ESI-MS: m/z=534 [M+H]$^+$, Cl-Pattern

Example 38

(3R,4R)-1-Methanesulfonyl-pyrrolidine-3,4-dicarboxylic acid 3-(4-chloro-benzylamide) 4-{[2-fluoro-4-(2-oxo-2H-pyridin-1-yl)-phenyl]-amide}

The compound of example 38 was prepared according to the methods described for example 28. ESI-MS: m/z=547 [M+H]$^+$, Cl-Pattern

Example 39

(3R,4R)-1-Methanesulfonyl-pyrrolidine-3,4-dicarboxylic acid 3-[(4-chloro-phenyl)-amide] 4-{[2-fluoro-4-(3-methoxy-2-oxo-2H-pyridin-1-yl)-phenyl]-amide}

According to General Method 2e)

Step 1: (3R,4R)-Pyrrolidine-1,3,4-tricarboxylic acid-1-tert-butyl ester-3-ethyl ester 7a The stereoselective mono saponification of the racemic mixture of compound 1b to compound 7a and the correpsonding S,S-enantiomer is described in: R. M. Rodriguez Sarmiento, B. Wirz, H. Iding, Tetrahedron Asymmetry, 14, 2003, 1547-1551.

Step 2a: (3R,4R)-4-(4-Chlorophenylcarbamoyl)-pyrrolidine-1,3-dicarboxylic acid 1-tert-butyl ester-3-ethyl ester 39b Compound 7a (1 g; 3.48 mmol) is suspended in acetonitrile (7 ml) and N,N-diisopropyl ethyl amin (1.22 ml; 6.96 mmol) is added at 25° C. BOP-Cl (1.772 g; 6.96 mmol) is added as a solid and after stirring for 30 min at 25° C. 4-chloroaniline (0.444 g; 3.48 mmol) is added to the reaction mixture. The mixture is stirred for 18 h at 25° C., evaporated to dryness and dissolved in ethyl acetate (100 ml). The organic phase is washed with saturated aquous Na$_2$CO$_3$ solution (100 ml), 2 N HCl (50 ml), water and brine and dried over Na$_2$SO$_4$. The organic phase is filtered and the filtrate is evaporated to dryness. The crude product is purified by silica gel chromatography. Yield: 0.5 g (36.2%), ESI-MS: m/z=395 [M−H]$^-$, Cl-pattern Step 3: (3R,4R)-4-(4-Chloro-phenylcarbamoyl)-pyrrolidine-3-carboxylic acid ethyl ester hydrochloride 39c Compound 39b (1.6 g; 4.03 mmol) is dissolved in 6N HCl in isopropanol (12.5 ml) and the reaction mixture is stirred for 2 h at 25° C. The reaction mixture is evaporated to dryness and the crude product is crystallized twice from diethylether to yield an off-white solid. Yield: 1.44 g (107.2%), ESI-MS: m/z=297 [M+H]$^+$, Cl-Pattern Step 4: (3R,4R)-4-(4-Chloro-phenylcarbamoyl)-1-methanesulfonyl-pyrrolidine-3-carboxylic acid ethyl ester 39d Compound 39c (1.44 g; 4.32 mmol) is dissolved in acetonitrile (10 ml) under addition of N,N-diisopropyl ethyl amine (2200 µl; 12.96 mmol). Methanesulfonylchloride (990 mg; 8.64 mmol) is added and the mixture is stirred for 18 h at 25° C. The reaction mixture is evaporated to dryness and purified with silica gel chromatography. Yield: 0.895 g (55.3%), ESI-MS: m/z=375 [M+H]$^+$, Cl-pattern Step 5: (3R,4R)-4-(4-Chloro-phenylcarbamoyl)-1-methanesulfonyl-pyrrolidine-3-carboxylic acid 39e Compound 39d (0.9 g; 2.4 mmol) is dissolved in a mixture of 1,4-dioxane/water (1:1; 15 ml). LiOH monohydrate (0.302 g; 7.2 mmol) is added as a solid and the mixture is stirred for 18 at 25° C. The mixture is evaporated to dryness and dissolved in ethyl acetate and the product is extracted with saturated aqueous Na₂CO₃ solution. The aqueous phase is cooled to 10° C. and acidified with 25% aqueous HCl solution until pH=1. The product is extracted several times with ethylacetate (3×100 ml). The combined organic phases are washed with brine and dried over Na₂SO₄. After filtration the organic phase is evaporated to dryness. Yield: 0.7 g (84.1%), ESI-MS: m/z=345 [M–H]⁻, Cl-pattern Step 6: 1-(4-Amino-3-fluoro-phenyl)-3-methoxy-1H-pyridin-2-one 39f Compound 40f is prepared as described for compound 1e. ESI-MS: m/z=345 [M–H]⁻

Step 7: (3R,4R)-1-Methanesulfonyl-pyrrolidine-3,4-dicarboxylic acid 3-[(4-chloro-phenyl)-amide] 4-{[2-fluoro-4-(3-methoxy-2-oxo-2H-pyridin-1-yl)-phenyl]-amide} 39g Compound 39e (80 mg; 0.23 mmol) is suspended in acetonitrile (1 ml) and N,N-diisopropyl ethyl amin (47 µl; 0.277 mmol) is added at 25° C. BOP-Cl (70.5 mg; 0.277 mmol) is added as a solid and after stirring for 30 min at 25° C. 1-(4-amino-3-fluoro-phenyl)-3-methoxy-1H-pyridin-2-one (53.9 mg; 0.23 mmol) is added to the reaction mixture. The mixture is stirred for 3 d at 25° C., evaporated to dryness and purified by preparative HPLC. Yield: 1.9 mg (1.5%), ESI-MS: m/z=562 [M+H]⁺

Example 40

(3R,4R)-1-Methanesulfonyl-pyrrolidine-3,4-dicarboxylic acid 3-[(4-chloro-phenyl)-amide] 4-{[2,6-difluoro-4-(2-oxo-2H-pyridin-1-yl)-phenyl]-amide}

The compound of example 40 and 1-(4-Amino-3,5-difluoro-phenyl)-3-methoxy-1H-pyridin-2-one were prepared according to the methods described for example 39. ESI-MS: m/z=550 [M+H]⁺

Example 41

(3R,4R)-1-Methanesulfonyl-pyrrolidine-3,4-dicarboxylic acid 3-[(4-chloro-phenyl)-amide] 4-{[2-fluoro-4-(6-oxo-6H-pyridazin-1-yl)-phenyl]-amide}

The compound of example 41 and 2-(4-amino-3-fluoro-phenyl)-2H-pyridazin-3-one were prepared according to the methods described for example 39. ESI-MS: m/z=533 [M+H]⁺

Example 42

(3R,4R)-1-Methanesulfonyl-pyrrolidine-3,4-dicarboxylic acid 3-[(4-chloro-phenyl)-amide] 4-{[2-fluoro-4-(2-oxo-piperidin-1-yl)-phenyl]-amide}

The compound of example 42 and 1-(4-amino-3-fluoro-phenyl)-piperidin-2-one were prepared according to the methods described for example 39. ESI-MS: m/z=536 [M+H]⁺, Cl-pattern

Example 43

(3R,4R)-1-Methanesulfonyl-pyrrolidine-3,4-dicarboxylic acid 3-[(4-chloro-phenyl)-amide] 4-[(3-fluoro-4-morpholin-4-yl-phenyl)-amide]

The compound of example 43 was prepared according to the methods described for example 39. 3-fluoro-4-morpholin-4-yl-phenylamine is commercially available. ESI-MS: m/z=525 [M+H]⁺, Cl-pattern

Example 44

(3R,4R)-1-Methanesulfonyl-pyrrolidine-3,4-dicarboxylic acid 3-[(4-chloro-phenyl)-amide] 4-{[3-fluoro-4-(2-methyl-imidazol-1-yl)-phenyl]-amide}

The compound of example 44 and 3-fluoro-4-(2-methyl-imidazol-1-yl)-phenylamine (CAS 209960-27-0) were prepared according to the methods described for example 39. ESI-MS: m/z=519 [M+H]⁺, Cl-pattern

Example 45

(3R,4R)-1-Methanesulfonyl-pyrrolidine-3,4-dicarboxylic acid 3-[(4-chloro-phenyl)-amide] 4-[(3-fluoro-4-[1,2,4]triazol-1-yl-phenyl)-hydroxy-amide]

The compound of example 45 was prepared according to the methods described for example 39. N-(3-Fluoro-4-[1,2,4]triazol-1-yl-phenyl)-hydroxylamine is prepared according to CAS: 181997-13-7. ESI-MS: m/z=523 [M+H]⁺, Cl-pattern

Example 46

(3R,4R)-1-Methanesulfonyl-pyrrolidine-3,4-dicarboxylic acid 3-{[2-fluoro-4-(2-oxo-2H-pyridin-1-yl)-phenyl]-amide} 4-[(4-methoxy-phenyl)-methyl-amide]

The compound of example 46 was prepared according to the methods described for example 28. ESI-MS: m/z=543 [M+H]⁺

Example 47

(3R,4R)-1-Methanesulfonyl-pyrrolidine-3,4-dicarboxylic acid 3-{[2-fluoro-4-(2-oxo-2H-pyridin-1-yl)-phenyl]-amide} 4-[(4-trifluoromethoxy-phenyl)-amide]

The compound of example 47 was prepared according to the methods described for example 28. ESI-MS: m/z=583 [M+H]⁺

Example 48

(3R,4R)-1-Methanesulfonyl-pyrrolidine-3,4-dicarboxylic acid 3-[(4-chloro-phenyl)-amide] 4-{[4-(2-oxo-2H-pyridin-1-yl)-phenyl]-amide}

The compound of example 48 was prepared according to the methods described for example 40. ESI-MS: m/z=514 [M+H]⁺

Example 49

(3R,4R)-1-Cyclopropylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 49 was prepared according to the methods described for example 24. ESI-MS: m/z=508 [M+H]$^+$

Example 50

(3R,4R)-1-Methanesulfonyl-pyrrolidine-3,4-dicarboxylic acid 3-[(4-chloro-phenyl)-amide] 4-[(3-fluoro-2'-methylsulfanyl-biphenyl-4-yl)-amide]

The compound of example 50 was prepared according to the methods described for example 7 using compound CAS 209732-08-1 as amine. ESI-MS: m/z=562 [M+H]$^+$

Example 51

(3R,4R)-1-Methanesulfonyl-pyrrolidine-3,4-dicarboxylic acid 3-[(2'-tert-butylsulfamoyl-3-fluoro-biphenyl-4-yl)-amide] 4-[(4-chloro-phenyl)-amide]

The compound of example 51 was prepared according to the methods described for example 7 using CAS 209919-51-7 as amine. ESI-MS: m/z=651 [M+H]$^+$

Example 52

(3R,4R)-1-Methanesulfonyl-pyrrolidine-3,4-dicarboxylic acid 3-[(4-chloro-phenyl)-amide] 4-{[5-(2-methanesulfonyl-phenyl)-pyridin-2-yl]-amide}

The compound of example 52 was prepared according to the methods described for example 7 using compound CAS 793650-93-8 as amine. ESI-MS: m/z=577 [M+H]$^+$

Example 53

(3R,4R)-1-Methanesulfonyl-pyrrolidine-3,4-dicarboxylic acid 3-[(4-chloro-phenyl)-amide] 4-{[2-fluoro-4-(3-methyl-2-oxo-2H-pyridin-1-yl)-phenyl]-amide}

The compound of example 53 was prepared according to the methods described for example 7. ESI-MS: m/z=547 [M+H]$^+$

Example 54

(3R,4R)-1-Methanesulfonyl-pyrrolidine-3,4-dicarboxylic acid 3-[(4-chloro-phenyl)-amide] 4-[(3-fluoro-2'-methanesulfonyl-biphenyl-4-yl)-amide]

The compound of example 54 was prepared by oxidation of the compound of example 50.

The compound of example 50 (39.53 mg; 0.07 mmol) is dissolved in ethyl acetate (2 ml) at 25° C. To this solution mCPBA (30.34 mg; 2.5 equivalents) is added slowly and the mixture is stirred at 25° C. for 18 h. Purification with prep. HPLC. Yield: 8.15 mg (19.6%).
ESI-MS: m/z=594 [M+H]$^+$

Example 55

(3R,4R)-3-(5-Chloro-pyridin-2-ylcarbamoyl)-4-[2-fluoro-4-(2-oxo-2H-pyridin-1-yl)-phenylcarbamoyl]-pyrrolidine-1-carboxylic acid tert-butyl ester 2-Chloro-5-aminopyridine (3.258 g; 25 mmol) is dissolved in toluene (100 ml) under argon atmosphere. Within 10 min a solution of AlMe$_3$ in toluene (2N, 12.8 ml) is added slowly. The mixture is stirred for 1 h at 25° C. Compound 28b (10 g, 21 mmol) is added in one portion and the reaction mixture is heated under reflux for 2 h. The obtained yellow suspension is cooled to 25° C. and diluted with THF (35 ml). For hydrolysis acetic acid (4.8 ml) is added and the suspension is stirred for 18 h. The obtained precipitate is filtered off, washed with toluene and TBME and dried in vacuo. Yield: 8.46 g (72%). ESI-MS: m/z=556 [M+H]$^+$

Example 56

(3R,4R)-1-Ethanesulfonyl-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}

The compound of example 56 was prepared according to the methods described for example 7 starting from compound of example 55. ESI-MS: m/z=547 [M+H]$^+$

Example 57

(3R,4R)-1-(2,2-Difluoroethyl)-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}

The compound of example 57 is prepared according to the methods described for example 24 with the exception of step 3 and step 4:

Step 3: (3R,4R)-pyrrolidine-3,4-dicarboxylic acid 3-[(5-chloropyridin-2-yl)-amide] 4-{[2-fluoro-4-(2-oxo-2H-pyridin-1-yl)-phenyl]-amide} (compound 57a)

The compound of example 55 (8.4 g; 15 mmol) is suspended in dioxane (50 ml) and 4N HCl in dioxane is added (50 ml). After stirring at 25° C. for 50 min Boc-cleavage is completed. The mixture is diluted with THF and neutralized with aqueous Na$_2$CO$_3$-solution. The free base (3R,4R)-pyrrolidine-3,4-dicarboxylic acid 3-[(5-chloropyridin-2-yl)-amide] 4-{[2-fluoro-4-(2-oxo-2H-pyridin-1-yl)-phenyl]-amide} is extracted several times with THF/dichloromethane (1:1 vol). The organic phase is washed with saturated aqueous NaCl-solution, dried over Na$_2$SO$_4$ and evaporated to dryness to yield 4.1 g (59.5%) of compound 57a. ESI-MS: m/z=455 [M+H]$^+$ Step 4: (3R,4R)-1-(2,2-Difluoroethyl)-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}

Compound 57a (0.41 g; 0.9 mmol) is dissolved in dichloromethane (4 ml) and DIEA (0.233 ml) is added. To this mixture trifluoro-methanesulfonic acid 2,2-difluoro-ethyl ester (0.338 mg; 1.6 mmol), dissolved in 1 ml dichloromethane, is added in one portion. The mixture is stirred at 25° C. for 72 h. The organic phase is then washed with

Example 58

(3R,4R)-1-Methanesulfonyl-pyrrolidine-3,4-dicarboxylic acid 3-[(4-chloro-phenyl)-amide] 4-{[4-(1,1-dioxo-[1,2]thiazinan-2-yl)-phenyl]-amide}

The compound of example 58 was prepared according to the methods described for example 7 with the amine CAS 37441-49-9. ESI-MS: m/z=555 [M+H]$^+$

Example 59

(3R,4R)-1-Methanesulfonyl-pyrrolidine-3,4-dicarboxylic acid 3-[(4-chloro-phenyl)-amide] 4-{[4-(1,1-dioxo-isothiazolidin-2-yl)-phenyl]-amide}

The compound of example 59 was prepared according to the methods described for example 7 with the amine CAS 90556-91-5. ESI-MS: m/z=541 [M+H]$^+$

Example 60

(3R,4R)-1-Methanesulfonyl-pyrrolidine-3,4-dicarboxylic acid 3-[(4-chloro-phenyl)-amide] 4-{[2-methyl-4-(2-oxo-2H-pyridin-1-yl)-phenyl]-amide}

The compound of example 60 was prepared according to the methods described for example 7 with the amine, 1-(4-amino-3-methyl-phenyl)-1H-pyridin-2-one. ESI-MS: m/z=529 [M+H]$^+$

Example 61

(3R,4R)-1-Methanesulfonyl-pyrrolidine-3,4-dicarboxylic acid 3-[(4-chloro-phenyl)-amide] 4-{[2-fluoro-4-(3-oxo-morpholin-4-yl)-phenyl]-amide}

The compound of example 61 was prepared according to the methods described for example 7 with CAS 742073-22-9. ESI-MS: m/z=539 [M+H]$^+$

Example 62

(3R,4R)-1-Isopropyl-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}

The compound of example 62 was prepared according to the methods described for example 27. ESI-MS: m/z=498 [M+H]$^+$

Example 63

(3R,4R)-1-(4-Fluoro-benzyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 63 was prepared according to the methods described for example 27. ESI-MS: m/z=563 [M+H]$^+$

Example 64

(3R,4R)-1-Methanesulfonyl-pyrrolidine-3,4-dicarboxylic acid 3-[(4-chloro-phenyl)-amide] 4-[(2-oxo-2H-[1,3']bipyridinyl-6'-yl)-amide]

The compound of example 64 was prepared according to the methods described for example 7 with the amine CAS 536747-63-4. ESI-MS: m/z=516 [M+H]$^+$

Example 65

(3R,4R)-1-Pyridin-2-ylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 65 was prepared according to the methods described for example 27. ESI-MS: m/z=546 [M+H]$^+$

Example 66

(3R,4R)-1-Pyridin-3-ylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 66 was prepared according to the methods described for example 27. ESI-MS: m/z=546 [M+H]$^+$

Example 67

(3R,4R)-1-Pyridin-4-ylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 67 was prepared according to the methods described for example 27. ESI-MS: m/z=546 [M+H]$^+$

Example 68

(3R,4R)-1-(2-Methoxy-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 68 was prepared according to the methods described for example 24. ESI-MS: m/z=513 [M+H]$^+$

Example 69

(3R,4R)-1-(2-Fluoro-1-methyl-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 69 was prepared according to the methods described for example 27. ESI-MS: m/z=515 [M+H]$^+$

Example 70

3-{(3R,4R)-3-(4-Chloro-phenylcarbamoyl)-4-[2-fluoro-4-(2-oxo-2H-pyridin-1-yl)-phenylcarbamoyl]-pyrrolidin-1-yl}-propionic acid methyl ester The compound of example 70 was prepared according to the methods described for example 24. ESI-MS: m/z=541 [M+H]$^+$

--- aqueous ammonium acetate and NaCl solution, dried over Na$_2$SO$_4$ and evaporated to dryness. The crude product is purified by flash chromatography over SiO$_2$. Yield: 0.299 g (63.8%). ESI-MS: m/z=519 [M+H]$^+$

Example 71

(3R,4R)-1-(3-Fluoro-oxetan-3-ylmethyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 71 was prepared according to the methods described for example 24 using 3-bromomethyl-3-fluoro-oxetane (compound 71 e) as alkylating agent. ESI-MS: m/z=543 [M+H]$^+$ Synthesis of 3-bromomethyl-3-fluoro-oxetane

3-Benzyloxy-2-methylene-1-propanol 71a

2-Methylene-propane-1,3-diol (2.2 g; 24.96 mmol)and dibutyltin oxide (6.85 g; 27.96 mmol) were refluxed in chloroform/methanol (100 ml 10:1) for 24 h to obtain a clear solution. The solvent was removed under reduced pressure to give the stannoxane derivative as a white solid. Cesium fluoride (7.25 g; 47.7 mmol) was added and the mixture was dried under high vacuum. To this reaction mixture, DMF (20 ml) and benzyl bromide (3.27 ml; 27.5 mmol) were added and the reaction mixture was stirred for 24 h at 25° C. After that, the reaction mixture was heated at 50° C. for 1 h. The mixture is cooled to 25° C. and diluted with ethyl acetate (100 ml) and water (2 ml). The reaction mixture is stirred vigorously for 30 min and then filtered through a pad of celite to remove dibutyltin oxide. The filtrate was washed with water and then with brine, dried over Na$_2$SO$_4$ and the solvent was removed under reduced pressure. The crude product was purified by silica gel column chromatography eluting with 20% ethyl acetate/hexane to yield 2.6 g (60%) compound 71a) as oil.

$^1$H-NMR (CDCl$_3$): δ 7.36-7.28 (m, 5H), 5.20 (s, 1H), 5.15 (s, 1H), 4.51 (s, 2H), 4.19 (s, 2H), 4.10 (s, 2H).

3-Bromo-2-fluoro-2-(benzyloxymethyl)propan-1-ol 71 b

A solution of 71 a) (3.9 g; 21.91 mmol) and triethylamine 3HF complex (5.29 g; 5.35 ml; 32.86 mmol) in dichloromethane (100 ml) was treated with NBS (4.28 g; 24.1 mmol) portion wise at −10° C. and stirred for 17 h. Subsequently, the mixture was poured into ice-water (100 ml) and neutralized with 25% aqueous ammonia. The organic layer was separated, washed with 0.1 N HCl, followed by 5% aqueous NaHCO3, dried and evaporated to dryness. The crude material was purified by silica gel chromatography (15% ethyl acetate/hexane) to give 2.54 g (42%) of 71 b.

$^1$H-NMR (CDCl$_3$): δ 7.37-7.30 (m, 5H), 4.58 (s, 2H), 3.89-3.63 (m, 6H), GC-MS: 276 (M$^+$).

3-Fluoro-3-(benzyloxymethyl)oxetane 71 c

A mixture of 71 b (10 g; 36.10 mmol) and potassium carbonate (29.9 g; 216.9 mmol)) in dry acetonitrile (200 ml) is refluxed for 72 h. After that the reaction mixture is extracted with ethyl acetate, washed with brine, dried over Na$_2$SO$_4$ and purified by silica gel column chromatography (10% ethyl acetate/hexane) to give 2.12 g (30%) of 71 c.

$^1$H-NMR (CDCl$_3$): δ 7.38-7.30 (m, 5H), 4.77 (dd, 2H), 4.58 (dd, 2H), 3.81 (s, 1H), 3.76 (s, 1H), GC-MS: 196 (M$^{+)}$

3-Fluoro-3-(hydroxymethyl)oxetane 71 d

A solution of 71 c (1.1 g; 5.61 mmol) in EtOH (10 ml) containing Pd/C (200 mg, 10%) and acetic acid (1 ml) was stirred for 24 h under hydrogen atmosphere (40 psi). The catalyst was filtered off and the filtrate was concentrated under reduced pressure to give compound 71 d (410 mg; 70%).

$^1$H-NMR (CDCl$_3$): δ 4.77 (dd, 2H), 4.57 (dd, 2H), 3.98 (s, 1H), 3.93 (s, 1H).

3-Bromomethyl-3-fluoro-oxetane 71 e

To a stirred solution of compound 71 d (500 mg; 4.72 mmol) CBr$_4$ (1.95 g; 5.89 mmol) in dichloromethane (7 ml) was added portion wise triphenylphosphine (1.85 g; 7.07 mmol) at 0° C. After complete addition, the reaction mixture was stirred for additional 2 h, diluted with pentane and washed with 5% aq NaHCO3, brine and dried over Na$_2$SO$_4$. The solvent was removed under atmospheric pressure to give compound 71 e (406 mg, 51%).

$^1$H-NMR (CDCl$_3$): δ 4.79 (dd, 2H), 4.56 (dd, 2H), 3.78 (s, 1H), 3.73 (s, 1H).

Example 72

2-{(3R,4R)-3-(4-Chloro-phenylcarbamoyl)-4-[2-fluoro-4-(2-oxo-2H-pyridin-1-yl)-phenylcarbamoyl]-pyrrolidin-1-ylmethyl}-cyclopropanecarboxylic acid ethyl ester The compound of example 72 was prepared according to the methods described for example 24. ESI-MS: m/z=581 [M+H]$^+$

Example 73

(3R,4R)-1-Thiophen-2-ylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 73 was prepared according to the methods described for example 27. ESI-MS: m/z=551 [M+H]$^+$

Example 74

(3R,4R)-1-Thiophen-3-ylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 74 was prepared according to the methods described for example 27. ESI-MS: m/z=551 [M+H]$^+$

Example 75

(3R,4R)-1-Cyanomethyl-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 75 was prepared according to the methods described for example 24. ESI-MS: m/z=494 [M+H]$^+$

Example 76

(3R,4R)-1-Methyl-pyrrolidine-3,4-dicarboxylic acid 3-[(4-chloro-phenyl)-methyl-amide] 4-{[2-fluoro-4-(2-oxo-2H-pyridin-1-yl)-phenyl]-methyl-amide}

The compound of example 76 was prepared according to the methods described for example 24. ESI-MS: m/z=494 [M+H]$^+$

Example 77

(3R,4R)-1-(2-Tetrazol-1-yl-acetyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 77 was prepared according to the methods described for example 13. ESI-MS: m/z=565 [M+H]$^+$

Example 78

(3R,4R)-1-(2-1H-Tetrazol-5-yl-acetyl)-pyrrolidine-3,4-dicarboxylic acid 3-[(4-chloro-phenyl)-amide] 4-{[2-fluoro-4-(2-oxo-2H-pyridin-1-yl)-phenyl]-amide}

The compound of example 78 was prepared according to the methods described for example 13. ESI-MS: m/z=565 [M+H]$^+$

Example 79

(3R,4R)-1-(2,2-Difluoro-ethyl)-pyrrolidine-3,4-dicarboxylic acid 3-[(6-chloro-pyridazin-3-yl)-amide] 4-{[2-fluoro-4-(2-oxo-2H-pyridin-1-yl)-phenyl]-amide}

The compound of example 79 was prepared according to the methods described for example 57. ESI-MS: m/z=521 [M+H]$^+$

Example 80

(3R,4R)-1-(2,2-Difluoro-ethyl)-pyrrolidine-3,4-dicarboxylic acid 3-[(5-chloro-pyrimidin-2-yl)-amide] 4-{[2-fluoro-4-(2-oxo-2H-pyridin-1-yl)-phenyl]-amide}

The compound of example 80 was prepared according to the methods described for example 57. ESI-MS: m/z=521 [M+H]$^+$

Example 81

(3R,4R)-1-(2,2-Difluoro-ethyl)-pyrrolidine-3,4-dicarboxylic acid 3-[(5-chloro-thiophen-2-yl)-amide] 4-{[2-fluoro-4-(2-oxo-2H-pyridin-1-yl)-phenyl]-amide}

The compound of example 81 was prepared according to the methods described for example 57. ESI-MS: m/z=525 [M+H]$^+$

Example 82

(3R,4R)-1-Methanesulfonyl-pyrrolidine-3,4-dicarboxylic acid 3-[(4-chloro-phenyl)-amide] 4-{[4-(3-oxo-morpholin-4-yl)-phenyl]-amide}

The compound of example 82 was prepared according to the methods described for example 7 using as amine CAS 438056-69-0. ESI-MS: m/z=521 [M+H]$^+$

Example 83

(3R,4R)-3-(5-Chloro-pyridin-2-ylcarbamoyl)-4-[2-fluoro-4-(2-oxo-2H-pyridin-1-yl)-phenylcarbamoyl]-pyrrolidine-1-carboxylic acid methyl ester The compound of example 83 was prepared according to the methods described for example 57 and 14. ESI-MS: m/z=514 [M+H]$^+$

Example 84

(3R,4R)-1-Trifluoromethyl-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}

The compound of example 84 was prepared according to the methods described for example 57. ESI-MS: m/z=524 [M+H]$^+$

Example 85

(3R,4R)-1-(2,2,2-Trifluoro-ethyl)-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}

The compound of example 85 was prepared according to the methods described for example 57. ESI-MS: m/z=538 [M+H]$^+$

Example A

Film coated tablets containing the following ingredients can be manufactured in a conventional manner:

| Ingredients | | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium Stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed:

1. A compound of the formula:

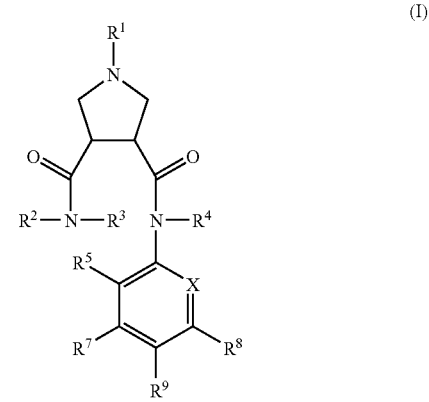

or a pharmaceutically acceptable salt thereof, wherein:

X is C—$R^6$;

$R^1$ is selected from the group consisting of: (1) hydrogen, (2) $C_{1-7}$ alkyl, (3) $C_{3-10}$ cycloalkyl, (4) $C_{3-10}$ cycloalkyl-$C_{1-7}$ alkyl, (5) fluoro-$C_{1-7}$ alkyl, (6) hydroxy-$C_{1-7}$ alkyl, (7) CN—$C_{1-7}$ alkyl, (8) hydroxy substituted fluoro-$C_{1-7}$ alkyl, (9) $C_{2-7}$ alkinyl, (10) $R^{10}C(O)$—, (11) $R^{10}OC(O)$—, (12) $N(R^{11},R^{12})C(O)$—, (13) $R^{10}OC(O)$—$C_{1-7}$ alkyl, (14) $N(R^{11},R^{12})C(O)$—$C_{1-7}$ alkyl, (15) $R^{10}$—$SO_2$, (16) $R^{10}$—$SO_2$—$C_{1-7}$ alkyl, (17) $N(R^{11},R^{12})$—$SO_2$, (18) $N(R^{11},R^{12})$—$SO_2$—$C_{1-7}$ alkyl, (19) aryl-$C_{1-7}$ alkyl, (20) heteroaryl, (21) heteroaryl-$C_{1-7}$ alkyl, (22) $C_{1-7}$ alkoxy-$C_{1-7}$ alkyl, (23) $C_{1-7}$ alkoxycarbonyl-$C_{3-10}$ cycloalkyl-$C_{1-7}$ alkyl, and (24) heterocyclyl-$C_{1-7}$ alkyl;

$R^2$ is hydrogen or $C_{1-7}$ alkyl;

$R^3$ is aryl, aryl-$C_{1-7}$ alkyl, heteroaryl or heteroaryl-$C_{1-7}$ alkyl;

$R^4$ is hydrogen, $C_{1-7}$ alkyl or hydroxy;

$R^5$, $R^6$, $R^7$ and $R^8$ independently from each other are selected from the group consisting: of (1) hydrogen, (2) halogen, (3) $C_{1-7}$ alkyl, (4) $C_{1-7}$ alkoxy, (5) fluoro-$C_{1-7}$ alkyl, (6) fluoro-$C_{1-7}$ alkyloxy, and (7) CN;

$R^9$ is aryl, heterocyclyl, heteroaryl or heterocyclyl-C(O)—;

$R^{10}$ is selected from the group consisting of: (1) hydrogen, (2) $C_{1-7}$ alkyl, (3) $C_{3-10}$ cycloalkyl, (4) $C_{3-10}$ cycloalkyl-$C_{1-7}$ alkyl, (5) hydroxy-$C_{1-7}$ alkyl, (6) fluoro-$C_{1-7}$ alkyl, (7) $C_{1-7}$ alkyl-$SO_2$—$C_{1-7}$ alkyl, (8) aryl, (9) aryl-$C_{1-7}$ alkyl, (10) heteroaryl, (11) heteroaryl-$C_{1-7}$ alkyl, and (12) heterocyclyl;

$R^{11}$ and $R^{12}$ independently from each other are selected from the group consisting of: (1) hydrogen, (2) $C_{1-7}$ alkyl, (3) hydroxy-$C_{1-7}$ alkyl, (4) fluoro-$C_{1-7}$ alkyl, (5) $C_{3-10}$ cycloalkyl, (6) $C_{3-10}$ cycloalkyl-$C_{1-7}$ alkyl, (7) aryl, (8) aryl-$C_{1-7}$ alkyl, (9) heteroaryl, and (10) heteroaryl-$C_{1-7}$ alkyl; or $R^{11}$ and $R^{12}$, together with the nitrogen atom to which they are attached, form a heterocyclic ring selected from the group consisting of: (1) piperidinyl, (2) piperazinyl, (3) morpholinyl, (4) pyrrolidinyl, (5) pyrrolinyl and (6) azetidinyl, which said heterocyclic ring can optionally be substituted with $C_{1-7}$ alkyl, halogen or hydroxy.

2. A compound of claim 1, wherein:
$R^1$ is selected from the group consisting of: (1) hydrogen, (2) $C_{1-7}$ alkyl, (3) $C_{3-10}$ cycloalkyl, (4) $C_{3-10}$ cycloalkyl-$C_{1-7}$ alkyl, (5) fluoro-$C_{1-7}$ alkyl, (6) hydroxy-$C_{1-7}$ alkyl, (7) CN—$C_{1-7}$ alkyl, (8) hydroxy substituted fluoro-$C_{1-7}$ alkyl, (9) $C_{2-7}$ alkinyl, (10) $R^{10}C(O)$—, (11) $R^{10}OC(O)$—, (12) $N(R^{11},R^{12})C(O)$—, (13) $R^{10}OC(O)$—$C_{1-7}$ alkyl, (14) $N(R^{11},R^{12})C(O)$—$C_{1-7}$ alkyl, (15) $R^{10}$—$SO_2$, $R^{10}$—$SO_2$—$C_{1-7}$ alkyl, (16) $N(R^{11},R^{12})$—$SO_2$, (17) $N(R^{11},R^{12})$—$SO_2$—$C_{1-7}$ alkyl, (18) aryl-$C_{1-7}$ alkyl, (19) heteroaryl, and (20) heteroaryl-$C_{1-7}$ alkyl; and
$R^{10}$ is selected from the group consisting of: (1) hydrogen, (2) $C_{1-7}$ alkyl, (3) $C_{3-10}$ cycloalkyl, (4) $C_{3-10}$ cycloalkyl-$C_{1-7}$ alkyl, (5) hydroxy-$C_{1-7}$ alkyl, (6) fluoro-$C_{1-7}$ alkyl, (7) $C_{1-7}$ alkyl-$SO_2$—$C_{1-7}$ alkyl, (8) aryl, (9) aryl-$C_{1-7}$ alkyl, (10) heteroaryl, and (11) heteroaryl-$C_{1-7}$ alkyl.

3. A compound of claim 2, having the formula:

(Ia)

or a pharmaceutically acceptable salt thereof, wherein $R^1$, $R^2$, $R^3$, $R^4$, $R^5$, $R^7$, $R^8$, $R^9$ and X are as defined in claim 2.

4. A compound of claim 3, wherein $R^1$ selected from the group consisting of: (1) hydrogen, (2) $C_{1-7}$ alkyl, (3) fluoro-$C_{1-7}$ alkyl, (4) hydroxy-$C_{1-7}$ alkyl, (5) CN—$C_{1-7}$ alkyl, (6) HC(O)—, (7) $C_{1-7}$ alkyl-C(O)—, (8) $C_{1-7}$ alkoxy-C(O)—, (9) $C_{1-7}$ alkoxy-C(O)—$C_{1-7}$ alkyl, (10) $NH_2$—C(O)—$C_{1-7}$ alkyl, (11) $C_{1-7}$ alkyl-NH—C(O)—$C_{1-7}$ alkyl, (12) $NH_2$—$SO_2$, (13) $C_{1-7}$ alkyl-$SO_2$, (14) fluoro-$C_{1-7}$ alkyl-$SO_2$, (15) $N(C_{1-7}$ alkyl$)_2$-$SO_2$, and (16) pyrrolidino-C(O)—.

5. A compound of claim 4, wherein $R^1$ is $C_{1-7}$ alkyl, fluoro-$C_{1-7}$ alkyl, $C_{1-7}$ alkyl-$SO_2$, fluoro-$C_{1-7}$ alkyl-$SO_2$, $N(C_{1-7}$ alkyl$)_2$-$SO_2$, $C_{1-7}$ alkoxy-C(O)— or HC(O)—.

6. A compound of claim 5, wherein $R^1$ is 2,2-difluoro-ethyl, ethanesulfonyl, methanesulfonyl, propylsulfonyl, isopropylsulfonyl, 2,2,2-trifluoro-ethylsulfonyl, isopropyl, $N(CH_3)_2$—$SO_2$, ethoxy-carbonyl or formyl.

7. A compound of claim 6, wherein $R^2$ is hydrogen.

8. A compound of claim 7, wherein $R^3$ is phenyl optionally substituted with 1 to 3 substituents selected from the group consisting of: (1) halogen, (2) $NH_2$, (3) $C_{1-7}$ alkoxy, and (4) fluoro-$C_{1-7}$ alkoxy, or $R^3$ is benzyl optionally substituted with halogen, or $R^3$ is pyridinyl optionally substituted with halogen, or $R^3$ is indolyl.

9. A compound of claim 8, wherein $R^3$ is phenyl substituted with halogen or $R^3$ is pyridinyl substituted with halogen.

10. A compound of claim 9, wherein $R^3$ is 4-chloro-phenyl or 5-chloro-pyridin-2-yl.

11. A compound of claim 10, wherein $R^4$ is hydrogen.

12. A compound of claim 1, wherein $R^5$, $R^6$, $R^7$ and $R^8$ independently from each other are selected from the group consisting of hydrogen and halogen.

13. A compound of claim 12, wherein $R^6$ is halogen and $R^5$, $R^7$ and $R^8$ are hydrogen.

14. A compound of claim 13, wherein $R^6$ is fluorine and $R^5$, $R^7$ and $R^8$ are hydrogen.

15. A compound of claim 14, wherein $R^9$ is aryl, heterocyclyl or heteroaryl.

16. A compound of claim 15, wherein $R^9$ is heteroaryl.

17. A compound of claim 16, wherein $R^9$ is selected from the group consisting of: (1) furyl, (2) pyridyl, (3) pyridazinyl, (4) oxo-pyridazinyl, (5) pyrimidinyl, (6) 2-oxo-pyridinyl, (7) 2-oxo-pyrimidinyl, (8) pyrazinyl, (9) thienyl, (10) isoxazolyl, (11) oxazolyl, (12) oxadiazolyl, (13) imidazolyl, (14) pyrrolyl, (15) pyrazolyl, (16) triazolyl, (17) tetrazolyl, (18) thiazolyl, (19) isothiazolyl, (20) 1,2,3-thiadiazolyl, (21) benzoimidazolyl, (22) indolyl, and (23) indazolyl.

18. A compound of claim 17, wherein $R^9$ is 2-oxo-2H-pyridin-1-yl.

19. A compound of claim 1, wherein said compound is selected from the group consisting of:
(3R,4R)-1-(2,2,2-Trifluoro-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide},
(3R,4R)-1-(2,2-Difluoro-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide},
(3R,4R)-1-Sulfamoyl-pyrrolidine-3,4-dicarboxylic acid 3-[(4-chloro-phenyl)-amide] 4-{[2-fluoro-4-(2-oxo-2H-pyridin-1-yl)-phenyl]-amide},
(3R,4R)-1-Ethanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide},
(3R,4R)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide},
(3R,4R)-1-Isopropyl-pyrrolidine-3,4-dicarboxylic acid 3-[(4-chloro-phenyl)-amide] 4-{[2-fluoro-4-(2-oxo-2H-pyridin-1-yl)-phenyl]-amide}, and
(3R,4R)-1-Methanesulfonyl-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}
and any pharmaceutically acceptable salts thereof.

20. A compound of claim 1 wherein said compound is selected from the group consisting of:
(3R,4R)-1-Methylcarbamoylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid methyl ester, (3R,4R)-1-(2-Hydroxy-ethyl)-pyrrolidine-3,4-dicarboxylic acid 3-[(4-chloro-phenyl)- amide] 4-{[2-fluoro-4-(2-oxo-2H-pyridin-1-yl)-phenyl]-amide}, trans-(3RS,4RS)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(4-chloro-phenyl)-amide] 4-{[2-fluoro-4-(3-methoxy-2-oxo-2H-pyridin-1-yl)-phenyl]-amide}, (3R,4R)-1-Acetyl-pyrrolidine-3,4-dicarboxylic acid 3-[(4-chloro-phenyl)-amide] 4-{[4-(3-methoxy-2-oxo-2H-pyridin-1-yl)-phenyl]-amide}, trans-(3RS,4RS)-1-Cyanomethyl-pyrrolidine-3,4-dicarboxylic acid 3-[(4-chloro-phenyl)- amide] 4-{[2-fluoro-4-(2-oxo-2H-pyridin-1-yl)-phenyl]-amide}, trans-(3RS,4RS)-1-Carbamoylmethyl-pyrrolidine-3,4-dicarboxylic acid 3-[(4-chloro-phenyl)-amide] 4-{[2-fluoro-4-(2-oxo-2H-pyridin-1-yl)-phenyl]-amide}, trans-(3RS,4RS)-1-(3,3,3-Trifluoro-propyl)-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Formyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(4-chloro-3-fluoro-phenyl)-amide] 4-{[2-fluoro-4-(2-oxo-2H-pyridin-1-yl)-phenyl]-amide}and (3R,4R)-1-Methanesulfonyl-pyrrolidine-3,4-dicarboxylic acid 3-[(4-chloro-2-fluoro-phenyl)-amide] 4-{[2-fluoro-4-(2-oxo-2H-pyridin-1-yl)-phenyl]-amide} and any pharmaceutically acceptable salts thereof.

21. A compound of claim 1 wherein said compound is selected from the group consisting of:

trans-(3RS,4RS)-{3-(4-Chloro-phenylcarbamoyl)-4-[2-fluoro-4-(2-oxo-2H-pyridin-1-yl)-phenylcarbamoyl]-pyrrolidin-1-yl}-acetic acid ethyl ester, (3R,4R)-1-Methanesulfonyl-pyrrolidine-3,4-dicarboxylic acid 3-[(3-fluoro-4-methoxy-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-{[2-fluoro-4-(2-oxo-2H-pyridin-1-yl)-phenyl]-amide} 4-[(1H-indol-5-yl)-amide], (3R,4R)-1-Methanesulfonyl-pyrrolidine-3,4-dicarboxylic acid 3-[(2-amino-4-chloro-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-{[2-fluoro-4-(2-oxo-2H-pyridin-1-yl)-phenyl]-amide} 4-[(4-methoxy-phenyl)-amide], (3R,4R)-1-Methanesulfonyl-pyrrolidine-3,4-dicarboxylic acid 3-[(4-chloro-phenyl)-amide] 4-[(3-fluoro-4-morpholin-4-yl-phenyl)-amide], (3S,4S)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(3-chloro-4-methoxy-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(4-chloro-phenyl)-methyl-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-{[2-fluoro-4-(2-oxo-2H-pyridin-1-yl)-phenyl]-amide} 4-[(1H-indazol-5-yl)-amide] and (3R,4R)-1-Methanesulfonyl-pyrrolidine-3,4-dicarboxylic acid 3-[(4-chloro-phenyl)-amide] 4-[(3-fluoro-4-[1,2,4]triazol-1-yl-phenyl)-hydroxy-amide]

and any pharmaceutically acceptable salts thereof.

22. A compound of claim 1 wherein said compound is selected from the group consisting of:

(3R,4R)-1-Methanesulfonyl-pyrrolidine-3,4-dicarboxylic acid 3-[(4-chloro-phenyl)-amide] 4-{[3-fluoro-4-(2-methyl-imidazol-1-yl)-phenyl]-amide}, (3R,4R)-Pyrrolidine-3,4-dicarboxylic acid 3-[(4-chloro-phenyl)-amide] 4-[(3-fluoro-2'-methylsulfanyl-biphenyl-4-yl)-amide], (3R,4R)-1-Methanesulfonyl-pyrrolidine-3,4-dicarboxylic acid 3-{[2-fluoro-4-(2-oxo-2H-pyridin-1-yl)-phenyl]-amide} 4-[(4-methoxy-phenyl)-methyl-amide], (3R,4R)-1-Methanesulfonyl-pyrrolidine-3,4-dicarboxylic acid 3-(4-chloro-benzylamide) 4-{[2-fluoro-4-(2-oxo-2H-pyridin-1-yl)-phenyl]-amide}, (3R,4R)-1-Methanesulfonyl-pyrrolidine-3,4-dicarboxylic acid 3-{[2-fluoro-4-(2-oxo-2H-pyridin-1-yl)-phenyl]-amide} 4-[(4-trifluoromethoxy-phenyl)-amide], (3R,4R)-1-(Propane-2-sulfonyl)-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-(2,2,2-Trifluoro-ethanesulfonyl)-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Dimethylsulfamoyl-pyrrolidine-3,4-dicarboxylic acid 3-[(4-chloro-phenyl)-amide] 4-{[2-fluoro-4-(2-oxo-2H-pyridin-1-yl)-phenyl]-amide} and (3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid ethyl ester and any pharmaceutically acceptable salts thereof.

23. A compound of claim 1 wherein said compound is selected from the group consisting of:

(3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid propyl ester, (3R,4R)-1-(Pyrrolidine-1-carbonyl)-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(4-chloro-phenyl)-amide] 4-{[2,6-difluoro-4-(2-oxo-2H-pyridin-1-yl)-phenyl]-amide}, (3R,4R)-1-Methanesulfonyl-pyrrolidine-3,4-dicarboxylic acid 3-[(4-chloro-phenyl)-amide] 4-{[2-fluoro-4-(6-oxo-6H-pyridazin-1-yl)-phenyl]-amide}, (3R,4R)-1-Methanesulfonyl-pyrrolidine-3,4-dicarboxylic acid 3-[(4-chloro-phenyl)-amide] 4-{[2-fluoro-4-(2-oxo-piperidin-1-yl)-phenyl]-amide}, (3R,4R)-1-Propanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}, and (3R,4R)-1-(2-Fluoro-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide} and any pharmaceutically acceptable salts thereof.

24. A compound of claim 1, wherein said compound is selected from the group consisting of:

(3R,4R)-1-(2,2-Difluoro-ethyl)-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Ethanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Isopropyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Methanesulfonyl-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}, (3R,4R)-1-Formyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-(Propane-2-sulfonyl)-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-(2,2,2-Trifluoro-ethanesulfonyl)-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-1-Dimethylsulfamoyl-pyrrolidine-3,4-dicarboxylic acid 3-[(4-chloro-phenyl)-amide] 4-{[2-fluoro-4-(2-oxo-2H-pyridin-1-yl)-phenyl]-amide}, (3R,4R)-3-(4-Chloro-phenylcarbamoyl)-4-[2-fluoro-4-(2-oxo-2H-pyridin-1-yl)-phenylcarbamoyl]-pyrrolidine-1-carboxylic acid ethyl ester, and (3R,4R)-1-Propanesulfonyl-pyrrolidine-3,4-dicarboxylic acid 3-[(4-chloro-phenyl)-amide] 4-{[2-fluoro-4-(2-oxo-2H-pyridin-1-yl)-phenyl]-amide}, and any pharmaceutically acceptable salts thereof.

25. A compound of claim 1, which is (3R,4R)-1-(2,2-Difluoroethyl)-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}.

26. A compound of claim 1, which is (3R,4R)-1-Isopropyl-pyrrolidine-3,4-dicarboxylic acid 3-[(5-chloro-pyridin-2-yl)-amide] 4-{[2-fluoro-4-(2-oxo-2H-pyridin-1-yl)-phenyl]-amide}.

27. A process for the manufacture of compounds of formula (I) as defined in claim 1, which process comprises a) reacting a compound of formula (II)

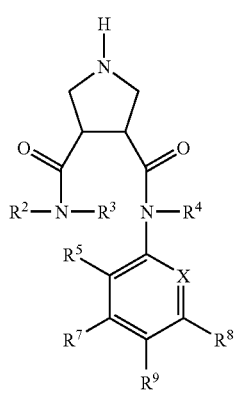

(II)

with a compound LG-R$^1$, or b) reacting a compound of formula (III)

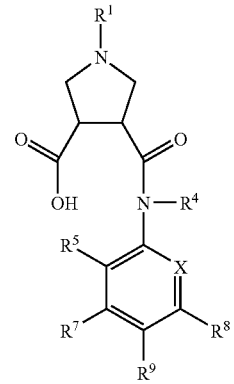

(III)

with a compound NHR$^2$R$^3$ or c) reacting a compound of formula (IV)

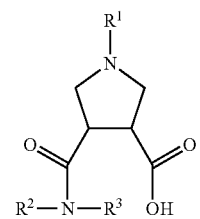

(IV)

with a compound of formula (V)

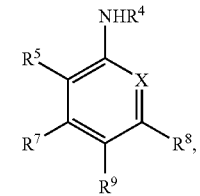

(V)

wherein R$^1$, R$^2$, R$^3$, R$^4$, R$^5$, R$^7$, R$^8$, R$^9$, and X have the significances given in claim 1 and LG is a leaving group.

28. The process of claim 27, which process comprises reacting a compound of formula (VI) or (VIII)

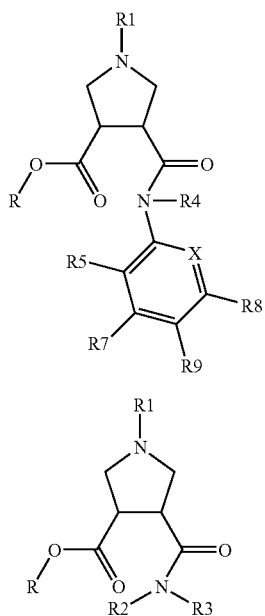

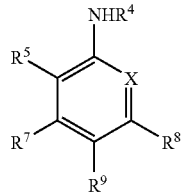

with a compound of formula (VII) or (V), respectively:

wherein $R^1$, $R^2$, $R^3$, $R^4$, $R^5$, $R^7$, $R^8$, $R^9$, and X have the significances given in claim 1, LG is a leaving group and R is $C_{1-7}$ alkyl, $C_{3-10}$ cycloalkyl or $C_{3-10}$ cycloalkyl-$C_{1-7}$ alkyl.

29. A pharmaceutical composition comprising a compound of claim 1, and a pharmaceutically acceptable carrier and/or adjuvant.

30. A compound of claim 1, which is
(3R,4R)-3-(5-Chloro-pyridin-2-ylcarbamoyl)-4-[2-fluoro-4-(2-oxo-2H-pyridin-1-yl)-phenylcarbamoyl]-pyrrolidine-1-carboxylic acid methyl ester.

\* \* \* \* \*